US 9,180,243 B2

(12) United States Patent
Michaud

(10) Patent No.: US 9,180,243 B2
(45) Date of Patent: Nov. 10, 2015

(54) DETECTION OF INFUSION PUMP CONDITIONS

(71) Applicant: Tandem Diabetes Care, Inc., San Diego, CA (US)

(72) Inventor: Michael Michaud, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 306 days.

(21) Appl. No.: 13/842,990

(22) Filed: Mar. 15, 2013

(65) Prior Publication Data

US 2014/0276538 A1   Sep. 18, 2014

(51) Int. Cl.
| | | |
|---|---|---|
| *A61M 5/145* | (2006.01) | |
| *A61M 5/142* | (2006.01) | |
| *A61M 5/168* | (2006.01) | |

(52) U.S. Cl.
CPC ....... *A61M 5/14244* (2013.01); *A61M 5/14216* (2013.01); *A61M 5/1684* (2013.01); *A61M 5/16831* (2013.01); *A61M 2005/14264* (2013.01); *A61M 2005/14268* (2013.01); *A61M 2205/3331* (2013.01); *A61M 2205/3351* (2013.01); *A61M 2205/3368* (2013.01); *A61M 2205/3372* (2013.01); *A61M 2205/3389* (2013.01); *A61M 2205/50* (2013.01); *A61M 2205/502* (2013.01); *A61M 2209/045* (2013.01)

(58) Field of Classification Search
CPC ............... A61M 2005/14268; A61M 5/14244; A61M 5/1456; A61M 5/16804; A61M 5/16854; A61M 5/1413; A61M 5/172; A61M 2005/16872; A61M 5/16859
See application file for complete search history.

(56) References Cited

U.S. PATENT DOCUMENTS

| | | |
|---|---|---|
| 722,431 A | 3/1903 | Packard |
| 1,274,884 A | 8/1918 | Hudson |
| 1,866,061 A | 7/1932 | Schoel |
| 2,412,397 A | 12/1946 | Harper |
| 2,971,466 A | 2/1961 | Corbett |
| 3,023,750 A | 3/1962 | Baron |
| 3,153,414 A | 10/1964 | Beall et al. |

(Continued)

FOREIGN PATENT DOCUMENTS

| | | |
|---|---|---|
| EP | 0272530 | 6/1988 |
| WO | WO9532013 A1 | 11/1995 |

(Continued)

OTHER PUBLICATIONS

PCT Search Report dated Jun. 8, 2014 for PCT Application No. PCT/US2014/021171 filed Mar. 6, 2014, 8 pages.

(Continued)

*Primary Examiner* — Scott Medway
(74) *Attorney, Agent, or Firm* — Patterson Thuente Pedersen, P.A.

(57) ABSTRACT

An ambulatory infusion system and a method of operating including a disposable infusion cartridge having a collapsible reservoir and a substantially rigid shell disposed over the collapsible reservoir having an interior volume, a pump device, a pressure sensor in communication with the interior volume and a processor. The method includes actuating the pressure sensor to take pressure measurements at regular time intervals; periodically assessing a preselected number of the pressure measurements with statistical analysis to identify statistical measures associated with the pressure measurements; and using the statistical measures to assess the status of the flexible reservoir and the pump device.

7 Claims, 16 Drawing Sheets

(56) References Cited

U.S. PATENT DOCUMENTS

| | | |
|---|---|---|
| 3,202,178 A | 8/1965 | Milton |
| 3,302,578 A | 2/1967 | Anderson |
| 3,493,496 A | 2/1970 | Bray et al. |
| 3,596,939 A | 8/1971 | Gibson |
| 3,838,794 A | 10/1974 | Cogley et al. |
| 3,985,133 A | 10/1976 | Jenkins et al. |
| 4,137,913 A | 2/1979 | Georgi |
| 4,271,989 A | 6/1981 | O'Neill et al. |
| 4,314,979 A | 2/1982 | Deabriges |
| 4,405,294 A | 9/1983 | Albarda |
| 4,416,596 A | 11/1983 | Lichtenstein |
| 4,443,218 A | 4/1984 | DeCant et al. |
| 4,636,226 A | 1/1987 | Canfora |
| 4,673,415 A | 6/1987 | Stanford |
| 4,808,167 A | 2/1989 | Mann et al. |
| 4,826,482 A | 5/1989 | Kamen |
| 4,886,499 A | 12/1989 | Cirelli et al. |
| 5,096,385 A * | 3/1992 | Georgi et al. .................. 417/18 |
| 5,170,912 A | 12/1992 | Du |
| 5,178,603 A | 1/1993 | Prince |
| 5,192,272 A | 3/1993 | Faure |
| 5,215,450 A | 6/1993 | Tamari |
| 5,295,976 A | 3/1994 | Harris |
| 5,364,242 A | 11/1994 | Olsen |
| 5,431,171 A | 7/1995 | Harrison et al. |
| 5,531,697 A | 7/1996 | Olsen et al. |
| 5,531,698 A | 7/1996 | Olsen |
| 5,568,806 A | 10/1996 | Cheney, II et al. |
| 5,647,854 A | 7/1997 | Olsen et al. |
| 5,704,520 A | 1/1998 | Gross |
| 5,891,097 A | 4/1999 | Saito et al. |
| 5,938,636 A | 8/1999 | Kramer |
| 5,984,894 A | 11/1999 | Poulsen et al. |
| 5,997,501 A | 12/1999 | Gross et al. |
| 6,093,312 A | 7/2000 | Boulter |
| 6,123,686 A | 9/2000 | Olsen et al. |
| D433,755 S | 11/2000 | Mastrotaro et al. |
| 6,213,120 B1 | 4/2001 | Block et al. |
| 6,280,408 B1 | 8/2001 | Sipin |
| 6,368,314 B1 * | 4/2002 | Kipfer et al. .................. 604/506 |
| 6,413,238 B1 | 7/2002 | Maget |
| 6,458,102 B1 | 10/2002 | Mann et al. |
| 6,520,936 B1 | 2/2003 | Mann |
| 6,641,533 B2 | 11/2003 | Causey et al. |
| 6,641,562 B1 | 11/2003 | Peterson |
| 6,676,387 B1 | 1/2004 | Penn |
| 6,743,201 B1 | 6/2004 | Doing et al. |
| 6,749,587 B2 | 6/2004 | Flaherty |
| 6,810,290 B2 | 10/2004 | Lebel et al. |
| 6,974,115 B2 | 12/2005 | Silva |
| 7,008,403 B1 | 3/2006 | Mallett |
| 7,029,455 B2 | 4/2006 | Flaherty |
| 7,107,706 B1 | 9/2006 | Bailey, Sr. et al. |
| 7,220,109 B2 | 5/2007 | Kultgen |
| 7,231,263 B2 | 6/2007 | Choi |
| 7,232,435 B2 | 6/2007 | Hildebrand et al. |
| 7,244,225 B2 | 7/2007 | Loeb et al. |
| 7,338,464 B2 | 3/2008 | Blischak et al. |
| 7,341,581 B2 | 3/2008 | Mallett |
| 7,374,556 B2 | 5/2008 | Mallett |
| 7,390,311 B2 | 6/2008 | Hildebrand et al. |
| 7,407,490 B2 | 8/2008 | Bendsen et al. |
| D598,109 S | 8/2009 | Collins et al. |
| D613,411 S | 4/2010 | Collins et al. |
| 7,811,279 B2 | 10/2010 | John |
| RE41,956 E | 11/2010 | Klitgaard et al. |
| 7,922,462 B2 | 4/2011 | Preuthun et al. |
| 7,935,104 B2 | 5/2011 | Yodfat et al. |
| 7,963,945 B2 | 6/2011 | Miller et al. |
| 7,967,022 B2 | 6/2011 | Grant et al. |
| 8,002,747 B2 | 8/2011 | Lord et al. |
| RE42,682 E | 9/2011 | Barreras, Sr. et al. |
| 8,032,226 B2 | 10/2011 | Miller et al. |
| RE42,958 E | 11/2011 | Loeb et al. |
| 8,056,582 B2 | 11/2011 | DiPerna |
| 8,062,257 B2 | 11/2011 | Moberg et al. |
| 8,066,629 B2 | 11/2011 | Dlugos |
| 8,094,009 B2 | 1/2012 | Allen et al. |
| 8,100,842 B2 | 1/2012 | Rousso |
| 8,105,265 B2 | 1/2012 | Demers et al. |
| 8,285,328 B2 | 10/2012 | Caffey et al. |
| 8,287,495 B2 | 10/2012 | Michaud et al. |
| 8,292,876 B2 | 10/2012 | Kriesel et al. |
| 8,298,183 B2 | 10/2012 | Menot et al. |
| 8,298,184 B2 | 10/2012 | DiPerna et al. |
| 8,328,754 B2 | 12/2012 | Estes et al. |
| 8,408,421 B2 | 4/2013 | DiPerna |
| 2001/0027791 A1 | 10/2001 | Wallace et al. |
| 2002/0040208 A1 | 4/2002 | Flaherty et al. |
| 2002/0072733 A1 | 6/2002 | Flaherty |
| 2003/0032930 A1 | 2/2003 | Branch et al. |
| 2003/0216683 A1 | 11/2003 | Shekalim |
| 2004/0122353 A1 | 6/2004 | Shahmirian et al. |
| 2004/0204673 A1 | 10/2004 | Flaherty |
| 2004/0260233 A1 | 12/2004 | Garibotto et al. |
| 2005/0004514 A1 | 1/2005 | Hochman |
| 2006/0150747 A1 | 7/2006 | Mallett |
| 2006/0150748 A1 | 7/2006 | Mallett |
| 2006/0206054 A1 | 9/2006 | Shekalim |
| 2006/0229557 A1 | 10/2006 | Fathallah et al. |
| 2006/0271022 A1 | 11/2006 | Steinbach et al. |
| 2007/0112301 A1 | 5/2007 | Preuthun et al. |
| 2007/0118405 A1 | 5/2007 | Campbell et al. |
| 2007/0250007 A1 | 10/2007 | Shekalim |
| 2007/0264130 A1 | 11/2007 | Mallett |
| 2008/0029173 A1 | 2/2008 | DiPerna |
| 2008/0051716 A1 | 2/2008 | Stutz |
| 2008/0058697 A1 | 3/2008 | Kamen et al. |
| 2008/0092969 A1 | 4/2008 | DiPerna |
| 2008/0196762 A1 | 8/2008 | Mallett |
| 2008/0234637 A1 | 9/2008 | McConnell et al. |
| 2009/0026146 A1 | 1/2009 | Carlisle et al. |
| 2009/0069785 A1 | 3/2009 | Miller et al. |
| 2009/0191067 A1 | 7/2009 | DiPerna |
| 2009/0192724 A1 | 7/2009 | Brauker et al. |
| 2009/0217982 A1 | 9/2009 | DiPerna |
| 2009/0254037 A1 | 10/2009 | Bryant et al. |
| 2009/0270833 A1 | 10/2009 | DeBelser et al. |
| 2009/0275896 A1 | 11/2009 | Kamen et al. |
| 2009/0287180 A1 | 11/2009 | Diperna |
| 2010/0008795 A1 | 1/2010 | DiPerna |
| 2010/0028208 A1 | 2/2010 | Shekalim et al. |
| 2010/0032041 A1 | 2/2010 | DiPerna |
| 2010/0036327 A1 | 2/2010 | DiPerna |
| 2010/0065578 A1 | 3/2010 | DiPerna |
| 2010/0065579 A1 | 3/2010 | DiPerna |
| 2010/0094114 A1 | 4/2010 | Robinson et al. |
| 2010/0096019 A1 | 4/2010 | DiPerna |
| 2010/0192686 A1 | 8/2010 | Kamen et al. |
| 2010/0218586 A1 | 9/2010 | Rosinko et al. |
| 2010/0324394 A1 | 12/2010 | Say et al. |
| 2011/0060280 A1 | 3/2011 | Caffey et al. |
| 2011/0120206 A1 | 5/2011 | Troughton et al. |
| 2011/0144586 A1 | 6/2011 | Michaud et al. |
| 2011/0144616 A1 | 6/2011 | Michaud et al. |
| 2011/0152770 A1 | 6/2011 | DiPerna |
| 2011/0152824 A1 | 6/2011 | DiPerna et al. |
| 2011/0160654 A1 | 6/2011 | Hanson et al. |
| 2011/0166544 A1 | 7/2011 | Verhoef et al. |
| 2011/0319862 A1 | 12/2011 | Friedman et al. |
| 2012/0029433 A1 | 2/2012 | Michaud et al. |
| 2012/0029468 A1 | 2/2012 | DiPerna et al. |
| 2012/0029708 A1 | 2/2012 | Miller et al. |
| 2012/0030610 A1 | 2/2012 | DiPerna et al. |
| 2013/0053816 A1 | 2/2013 | DiPerna et al. |
| 2013/0150766 A1 * | 6/2013 | Olde et al. .................. 604/4.01 |
| 2013/0204542 A1 * | 8/2013 | Olde et al. .................. 702/35 |
| 2013/0306191 A1 | 11/2013 | Metzmaker et al. |
| 2013/0324928 A1 | 12/2013 | Kruse |
| 2014/0039392 A1 | 2/2014 | Geipel et al. |
| 2014/0039805 A1 * | 2/2014 | Sharpe et al. .................. 702/24 |

(56) References Cited

U.S. PATENT DOCUMENTS

FOREIGN PATENT DOCUMENTS

| WO | WO0130422 | 5/2001 |
| WO | WO2004009160 | 1/2004 |
| WO | WO2007/065944 | 6/2007 |
| WO | WO2008/024812 | 2/2008 |
| WO | WO2009/016636 | 2/2009 |
| WO | WO2009044221 | 4/2009 |
| WO | WO2012019726 | 2/2012 |

OTHER PUBLICATIONS

International Search Report and Written Opinion for International Application No. PCT/US2014/021171 dated Jun. 8, 2014.
International Search Report and Written Opinion for International Application No. PCT/US2013/044259 dated Sep. 6, 2013.
European Search Report for European Application No. EP10805076 dated Mar. 18, 2013.
European Search Report for European Application No. EP09704892 dated Jan. 28, 2013.
Examination Report No. 1 for Australian Patent Application No. 2009249132 dated Jan. 23, 2014.
European Search Report for European Application No. 14152623.6-1506 dated Mar. 11, 2014.
Application and File History of U.S. Appl. No. 13/838,617, filed Mar. 15, 2013, inventor Kruse.
Application and File History of U.S. Appl. No. 12/468,795, filed May 19, 2009, inventor DiPerna.
Application and File History of U.S. Appl. No. 12/020,498, filed Jan. 25, 2008, inventor DiPerna.
Application and File History of U.S. Appl. No. 12/538,018, filed Aug. 7, 2009, inventor DiPerna.
Application and File History of U.S. Appl. No. 12/846,688, filed Jul. 29, 2010, inventor DiPerna.
Application and File History of U.S. Appl. No. 12/846,706, filed Jul. 29, 2010, inventor Michaud et al.
Application and File History of U.S. Appl. No. 12/846,720, filed Jul. 29, 2010, inventor DiPerna et al.
Application and File History of U.S. Appl. No. 12/846,733, filed Jul. 29, 2010 inventors Michaud et al.
Application and File History of U.S. Appl. No. 12/846,734, filed Jul. 29, 2010 inventors Verhoef et al.
Application and File History of U.S. Appl. No. 13/270,160, filed Oct. 10, 2011, inventor Michaud et al.
Application and File History of U.S. Appl. No. 13/271,156, filed Oct. 11, 2011, inventors DiPerna et al.
Application and File History of U.S. Appl. No. 13/273,484, filed Oct. 14, 2011, inventors DiPerna et al.
European Search Report for European Application No. EP09751416.0-2319 dated Nov. 21, 2012.
PCT Search Report dated Jun. 8, 2014 for PCT Application No. PCT/US2014/021171 filed Mar. 6, 2014, 13 pages.

* cited by examiner

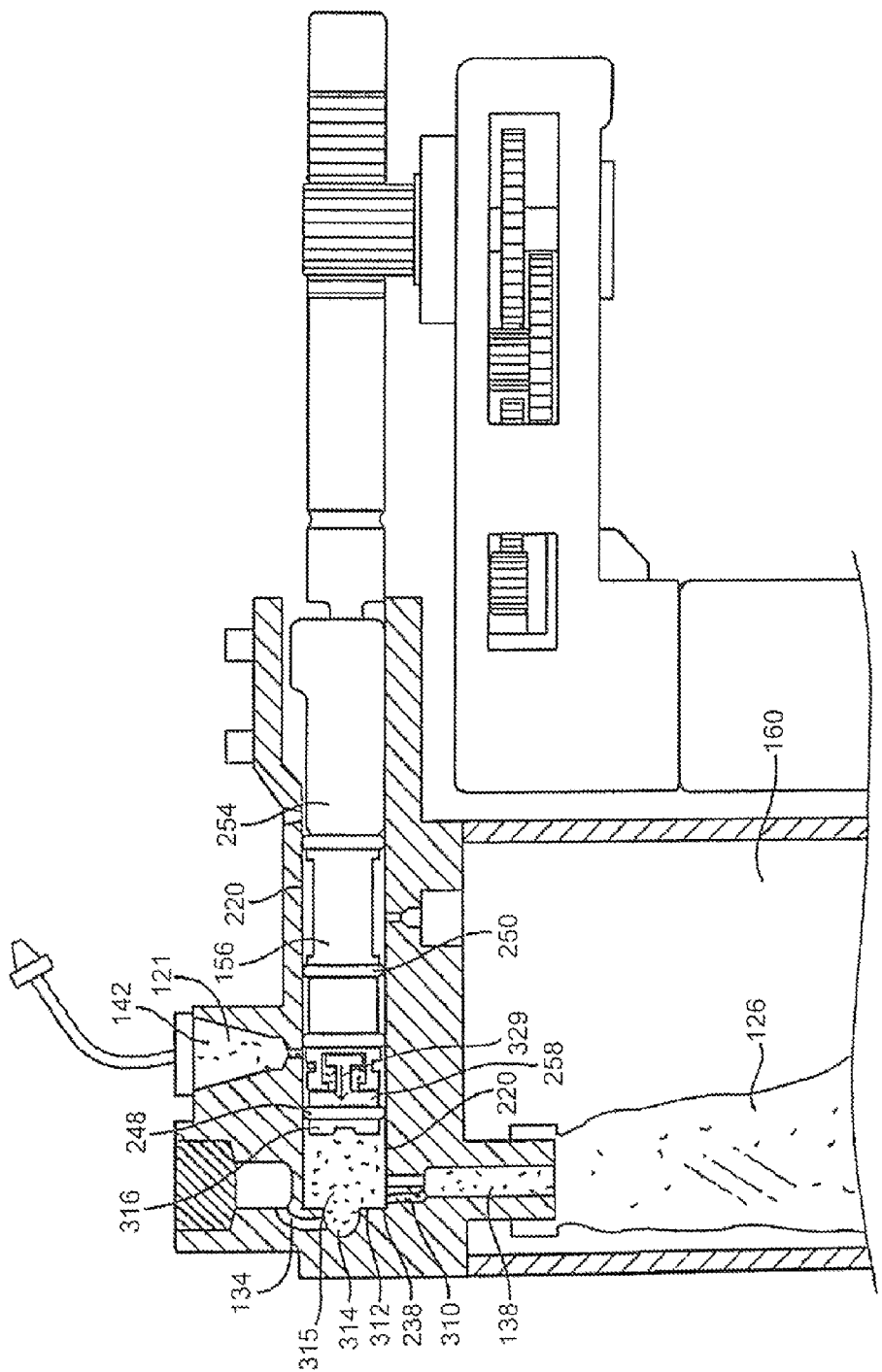

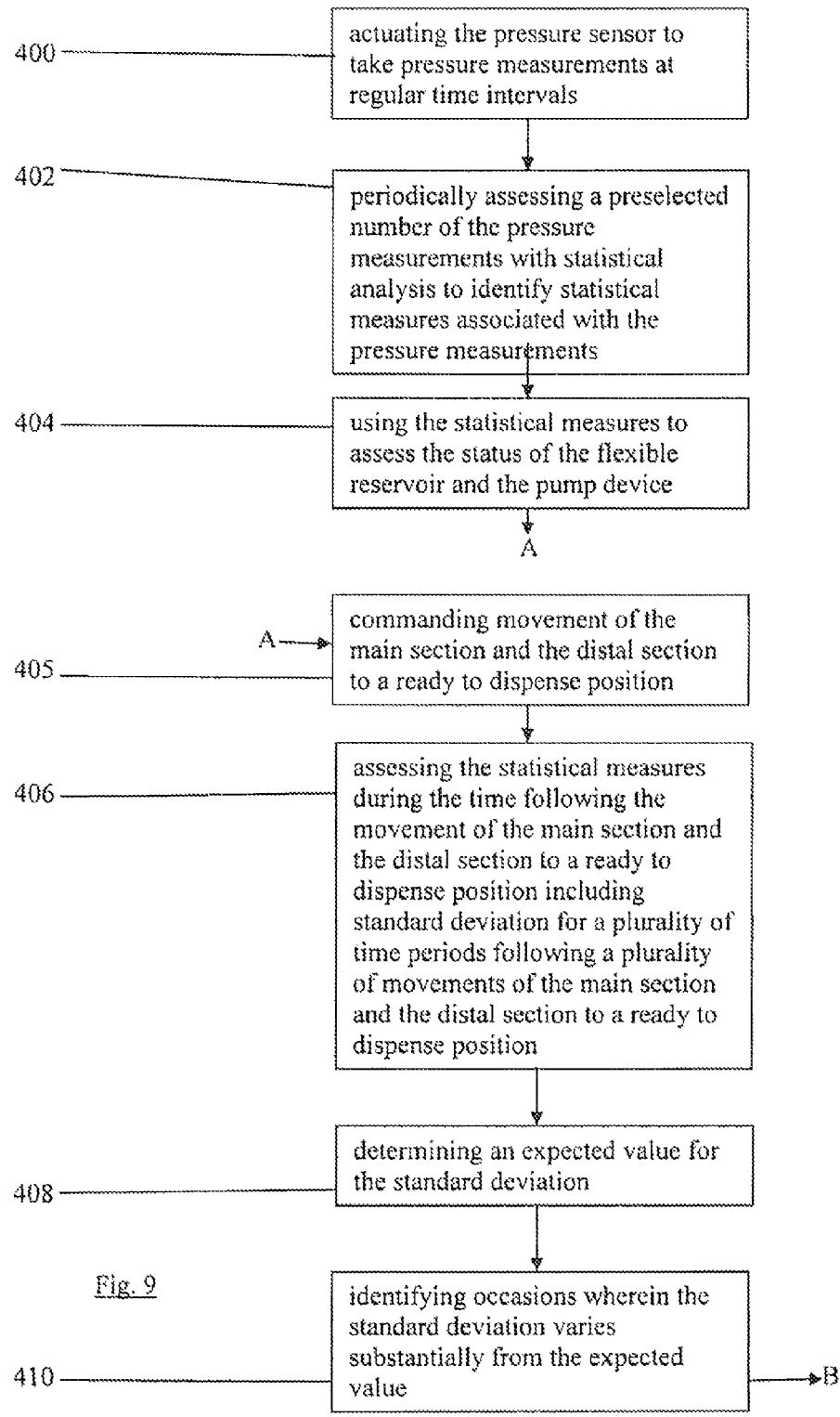

US 9,180,243 B2

DETECTION OF INFUSION PUMP CONDITIONS

FIELD OF THE INVENTION

The invention relates generally to infusion pumps that are utilized for example, in the treatment of diabetes. More particularly, the invention relates to infusion pumps that include a spool, a spool distal section, a collapsible reservoir, a vented volume and a pressure sensor and a controller in the design.

BACKGROUND OF THE INVENTION

Certain infusion pumps, particularly certain ambulatory insulin infusion pumps that are used to treat people having diabetes, include a spool with a distal section, a collapsible reservoir that contains insulin, vented volume surrounding the collapsible reservoir and a pressure sensor that senses the pressure within the vented volume. The pressure sensor is coupled to a controller or processor that is programmed with an algorithm to control, operate and monitor the infusion pump. The pressure sensor can be used to determine the fluid volume in the collapsible reservoir of the system. In such cases, pressure measurements are taken at intervals and variations in air pressure are used to calculate fluid volume within the collapsible reservoir.

One of the challenges of using the pressure sensor to determine fluid volume in the infusion pump system is that the related calculations are generally made under the assumption that the vented volume air pressure and the fluid pressure in the collapsible reservoir are the same. This assumption is not always true. This is due, for example, to the fact that the collapsible reservoir is not infinitely flexible, especially when it is filled to maximum or near maximum capacity. When the collapsible reservoir is filled to maximum capacity, the envelope of the collapsible reservoir is placed under stress and there can be variations between the pressure inside of the collapsible reservoir and the vented volume surrounding the collapsible reservoir. In the case of the collapsible reservoir being at or near maximum capacity, any compliance in the system, such as, e.g., air bubbles in the fluid or expansion of the fluid-containing structure that does not affect air chamber volume, can cause errors in the fluid volume measurement process as fluid that is removed from the collapsible reservoir in the system will not cause an equal change in air volume of the air in the air chamber.

SUMMARY OF THE INVENTION

The invention generally relates to ambulatory infusion devices and is particularly useful in ambulatory infusion devices used in the treatment of diabetes. Examples of such devices and various features that can be associated with such devices include those disclosed in U.S. patent application Ser. Nos. 13/557,163, 12/714,299, 12/538,018, U.S. Provisional Patent Application No. 61/655,883, U.S. Provisional Patent Application No. 61/656,967 and U.S. Pat. No. 8,287,495, each of which is incorporated herein by reference.

Certain infusion pumps, particularly, e.g., certain ambulatory insulin pumps that are used to treat people having diabetes, include a spool with a distal section, a collapsible reservoir that contains insulin, vented volume surrounding the collapsible reservoir and a pressure sensor that senses the pressure within the vented volume. The pressure sensor is coupled to a controller or processor that is programmed with an algorithm to control, operate and monitor the infusion pump. The pressure sensor can be used to determine the fluid volume in the collapsible reservoir of the system.

In the case of a collapsible reservoir being filled to or near to its maximum level or capacity, when the spool moves to the ready to dispense (RTD) position, there is a period of time after the move during which pressure readings indicating the pressure within the vented volume are variable before the pressure readings stabilize. This phenomenon has been observed to be significantly more pronounced in the case of a maximally-filled collapsible reservoir. Furthermore, this phenomenon can be detected by taking pressure readings directly after the spool move and observing the variability of the pressure readings such as by calculation of the standard deviation of the mean of the pressure reading samples as compared to the standard deviation of the pressure reading(s) sampled under other conditions.

One possible explanation for this phenomenon is that adiabatic heating and cooling of the fluid within the pump may occur. Adiabatic heating and cooling occur when, in a thermodynamically isolated system such as may be approximated by this system within the pump, a fluid experiences changes in pressure and the temperature of the fluid changes without any heat transfer taking place between the system and its surroundings.

According to one embodiment of the invention, detection of the vented volume pressure variation, or detection of pressure fluctuation followed by the relative stabilization of the pressure using, e.g., the air pressure sensor, is used to determine if the collapsible reservoir has attained a maximally-filled state.

According to the invention, these variations in vented volume pressure can also be utilized in potentially advantageous ways to estimate when the collapsible reservoir is full or near full, for occlusion detection, for fluid reservoir pressure assessment and for minimum prime amount determination. The observation of pressure may also be useful for determining other factors. In particular, there is a potential to avoid false occlusion detection that occurs due to a phenomenon known as "autodispensing". Autodispensing will be further discussed herein below.

According to an example embodiment of the invention, the estimation of the fluid volume may be impacted by external factors including temperature change transients and mechanical pressure that might be applied to the rigid container that encloses the vented volume as well as other factors. Measurement and identification of the variance in the pressure signals due to these external influences may be utilized to detect and identify external influences and presents an opportunity to reject these as misleading measurements or at least to, e.g., assign them a lower decision weight when using them to filter out such influences that may otherwise give false readings of dispense volume and other related measurements.

According to an embodiment, an infusion pump for dispensing a quantity of liquid has a spool, spool distal section, collapsible reservoir, vented volume and a pressure sensor. During normal operation, when the spool is moved, the spool distal section remains stationary and fluid is dispensed from the pump, through the patient infusion line and, ultimately, to the patient. If the collapsible reservoir is filled to or near its maximum level or capacity, the envelope of the collapsible reservoir will be under tension, and the fluid pressure of the collapsible reservoir may be high enough to result in a force on the spool distal section which exceeds the friction force between the spool distal section seal and the bore. In this case, the spool distal section will move toward the spool and there will be an "auto-dispense", or unintended dispensing of a volume of insulin, from the pump into the patient infusion line.

According to another embodiment of the invention, the air pressure in the vented volume is monitored by the pressure sensor directly before a movement of the spool at the ready to fill (RTF) position and RTD position as well as directly after a dispense move of the spool at each of the RTD and RTF positions. Pressure measurements can be made at the ready to fill position as well as at the filled position prior to beginning movement to the ready to dispense position. Thus, four pressure average measurements are recorded, one during a period before the spool is located at the RTF position, one after the spool is located at the RTF position and one each before and after the spool is at the RTD position. Thus, according to the invention, three volume measurements can be calculated by comparison of the four pressure measurements. By comparison of some or all of the three volume measurements the present invention determines if autodispensing did occur. Comparison of the volume measurements is well-suited for fill estimation of the collapsible reservoir, occlusion detection, fluid reservoir pressure assessment and minimum prime amount determination as well as other factors. Embodiments of the invention are also well-suited to avoid false occlusion detection due to autodispensing. Each pressure measurement is an average pressure measurement based on a series of momentary pressure measurements that are taken at short intervals and averaged periodically. For example, according to one embodiment, momentary pressure measurements are taken at a rate of eight per second and averaged for each second. Various conditions can be inferred from statistical analysis of these momentary pressure measurements, including but not limited to the collapsible reservoir being filled to or near to maximum capacity and whether autodispensing has occurred or is likely to occur.

Sequential air pressure measurements can be made by a pressure sensor that is in fluid communication with the vented volume in which the collapsible reservoir is housed. Air pressure measurements can be made regularly over a defined period of time within which period the average air pressure within the vented volume is taken periodically. These pressure samples can also be subjected to other statistical analyses. For example, according to one example embodiment of the invention, air pressure measurements are made at a rate of eight hertz (eight samples per second) and averaged each second.

The controller of the insulin pump, according to an embodiment, can be programmed to identify a standard deviation of the air pressure measurements over the selected period of time. For example, the average air pressure measurement may be taken at a rate of eight measurements per second and the standard deviation of the eight pressure measurement calculated as well. These values are exemplary and should not be considered limiting.

Accordingly, when the collapsible reservoir is filled to its maximum volume, advantage can be taken of the fact that there is a period of time directly after the movement of the spool during which the pressure is variable and finally stabilizes. Thus, according to the present invention the point at which the collapsible reservoir is filled to a maximum level or to about a maximum level can be identified by analyzing the standard deviation of a particular time period for sampling of air pressure. If the standard deviation in air pressure during the time period exceeds a threshold value it can be inferred that the collapsible reservoir is filled to or near its maximum level or capacity.

Thus, having captured this information, it is possible for the controller of the insulin pump to identify a filled state of the collapsible reservoir as well as detection of a false indication of an infusion obstruction if the collapsible reservoir is fully filled and autodispensing has occurred.

Further, the estimation of fluid volume can be altered by external influences such as temperature transients and mechanical pressure on the exterior of the rigid container that houses the vented volume. Measurements of the variance of pressure signals that are not associated with a collapsible reservoir that is filled may be used, according to an embodiment, to detect these internal influences and either reject measurements that are associated with them or assign the measurements associated with high variance a lower weight in the analysis process.

With regard to detection of autodispensing, according to an embodiment, when the spool and spool distal section are in the ready to fill (RTF) position, a pressure measurement can be taken by the pressure sensor. After the spool has transitioned from the RTF to the filled position, another pressure measurement is taken via the pressure sensor. Under normal conditions the volume of the collapsible reservoir will have decreased and the pressure within the air chamber will have dropped. The spool will then continue moving to the ready to dispense (RTD) position. During this time period, pressure measurements would continue to drop as insulin leaves the collapsible reservoir to fill in the space behind the spool distal section as the spool and spool distal section move from the filled position to the RTD position. While the spool and spool distal section are at rest in the RTD position, pressure within the air chamber under most circumstances will remain approximately constant. However, if the collapsible reservoir is filled at or near capacity and the envelope of the collapsible reservoir is under tension, a phenomenon known as "autodispensing" may occur. In the case of autodispensing, pressure of the fluid behind the spool distal section overcomes the frictional resistance of the spool distal section Seal, causing the spool distal section to move toward the spool, thus "autodispensing" a measured quantity of insulin. At this point, there is a reduction in pressure within the collapsible reservoir as the spool distal section moves toward the spool. This otherwise unexpected drop in pressure then can be identified as the result of autodispensing having occurred. Further, if autodispensing has not occurred, if the dispensing command is given and the spool moves toward the spool distal section normally there would be no change in pressure in the collapsible reservoir or the vented volume because the spool distal section remains stationary. In the case in which autodispensing has already occurred, there is a rise in pressure in the collapsible reservoir and a consequent rise in pressure in the air chamber, thus indicating that autodispensing has previously occurred. This can be used to confirm an earlier observation of autodispensing.

According to one embodiment of the invention, an alarm signal or message can be sent to the screen of the insulin pump to advise the patient that the collapsible reservoir has been filled to or near its maximum level or capacity and that autodispensing has occurred because of this phenomenon. The patient or caregiver then has the opportunity to take these issues into account at future fillings of the collapsible reservoir. The patient or caregiver can then take steps to avoid maximal filling of the collapsible reservoir.

According to an embodiment of the invention, a first pressure measurement is taken when the spool and distal section are at the RTF or filled position. This pressure is designated P1 also designated Prtf in Equation 1). The spool and distal section are then moved to the RTD position. This movement causes a change in volume referred to as Delta V1. A second pressure measurement is then taken when the spool and distal section are at the RTD position. This pressure is designated P2 (also designated Prtd in Equations 1 and 3). The spool is then moved from the RTD position to the dispensed position. This movement causes a change in volume referred to as Delta V2. A third pressure measurement is taken at the dispensed position. This pressure is designated P3 (also designated Pdispensed in Equation 3). The spool and distal extension are moved from the dispensed position back to the RTF position. A fourth pressure measurement is taken at the RTF position. This pressure is designated P4 (also designated Prtf in Equation 3).

With knowledge of the estimated pressures and volume changes, various calculations can be made.

A first estimate of air volume in the vented volume can be estimated from P1, Delta V1 and P2. Once the air volume is known, fluid volume within the collapsible reservoir, fluid passages and the bore can be estimated by subtraction of the air volume from the total known volume. The resulting fluid volume is designated Volume estimate1.

$$VRTF1 = \frac{Prtd * DeltaV1}{Prtf - Prtd} = \text{volume of air in the system when the spool is in the "RTF" position} \quad \text{(Equation 1)}$$

$$\text{Volume } estimate1 = Vinsulin = 4100\mu l - VRTF1 \quad \text{(Equation 2)}$$

Wherein 4100 µl is the assumed air volume of the system when the collapsible reservoir is empty.

If the second pressure equals the third pressure (P2=P3) the infusion pump is operating properly because during normal dispensing the spool distal section remains stationary during dispensing. If the second pressure is less than the third pressure (P2<P3) it can be inferred that either there is an occlusion in the fluid dispensing port or line or that autodispensing has occurred. This is because the spool distal section has moved distally thus increasing P3.

A second estimate of air volume in the vented volume can be estimated from P3, Delta V2 and P4. Once the air volume is known, fluid volume within the collapsible reservoir, fluid passages and the bore can be estimated by subtraction of the air volume from the total known volume. The resulting fluid volume is designated Volume estimate2.

$$VRTF2 = \frac{Pdispensed * DeltaV3}{Prtf - Pdispensed} = \text{volume of air in the system when the spool is in the "RTF" position} \quad \text{(Equation 3)}$$

$$\text{Volume } estimate2 = Vinsulin = 4100\mu l - VRTF2 \quad \text{(Equation 4)}$$

Based on the above information the following can be estimated:

If the second pressure equals the third pressure (P2=P3), the infusion pump is operating normally as expected.

If the second pressure is less than the third pressure (P2<P3) and Volume estimate1 is less than Volume estimate2, the infusion pump has autodispensed because the fill estimate has decreased.

If the second pressure is less than the third pressure (P2<P3) and Volume estimate1 is equal to Volume estimate2, there is an occlusion in the fluid dispensing port or line because the fill estimate is not decreasing. Thus, insulin is not being dispensed.

According to another embodiment, a persistence filter is included in the method so that the process is repeated a number of times before a determination is made that autodispensing has occurred or that an occlusion exists. If the process is repeated the designated number of times and it is estimated that autodispensing has occurred or that an occlusion exists the method includes presenting a message, alarm or warning that that autodispensing has occurred or that an occlusion exists as appropriate.

BRIEF DESCRIPTION OF THE DRAWINGS

FIG. 8 is similar to FIG. 2, but depicting a condition of an occlusion present in the delivery line.

DETAILED DESCRIPTION

Provided herein are systems, devices and methods for detecting auto dispensing and false signals related to temperature transients and mechanical forces applied to the infusion cartridge as well as detection of whether a collapsible insulin reservoir is at or near its maximum capacity in an infusion pump and particularly in an insulin pump. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

Figure 1A:
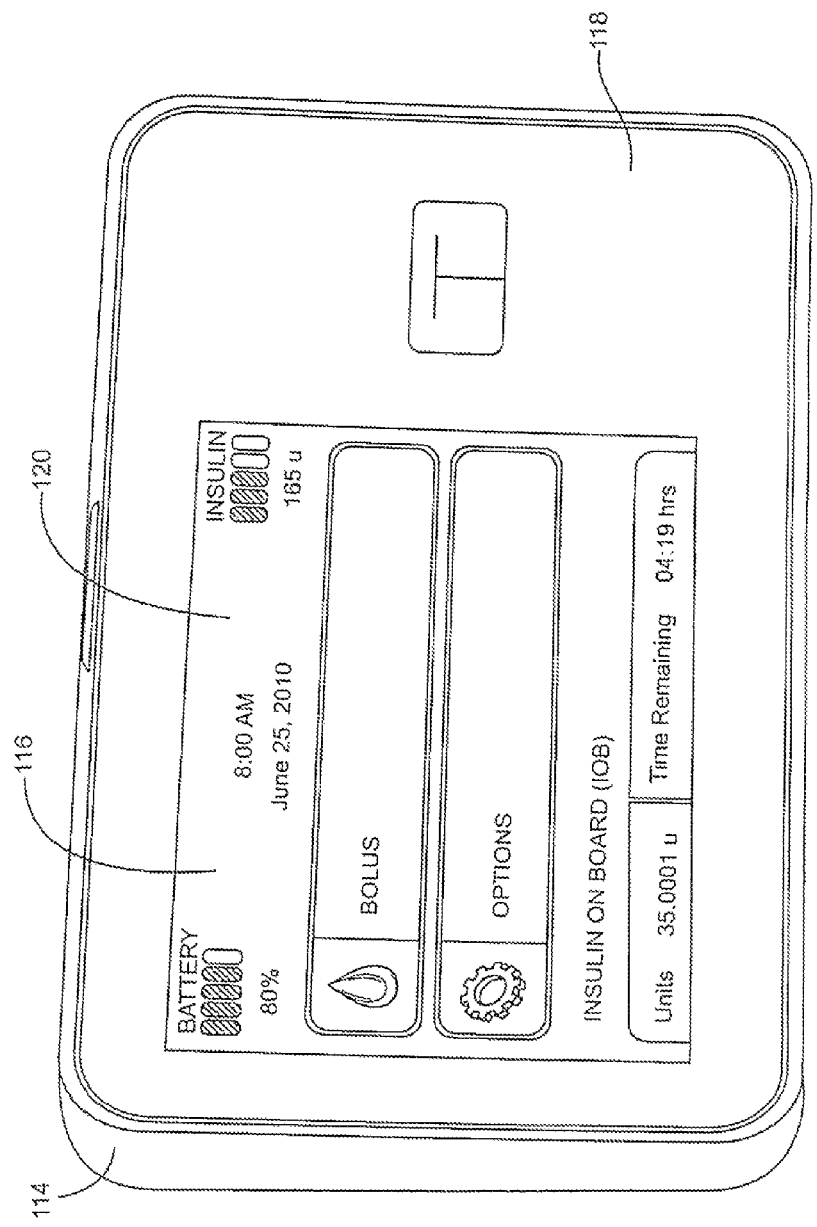
FIG. 1A is a front perspective view of an embodiment of a portable infusion pump system.
Figure 1B:
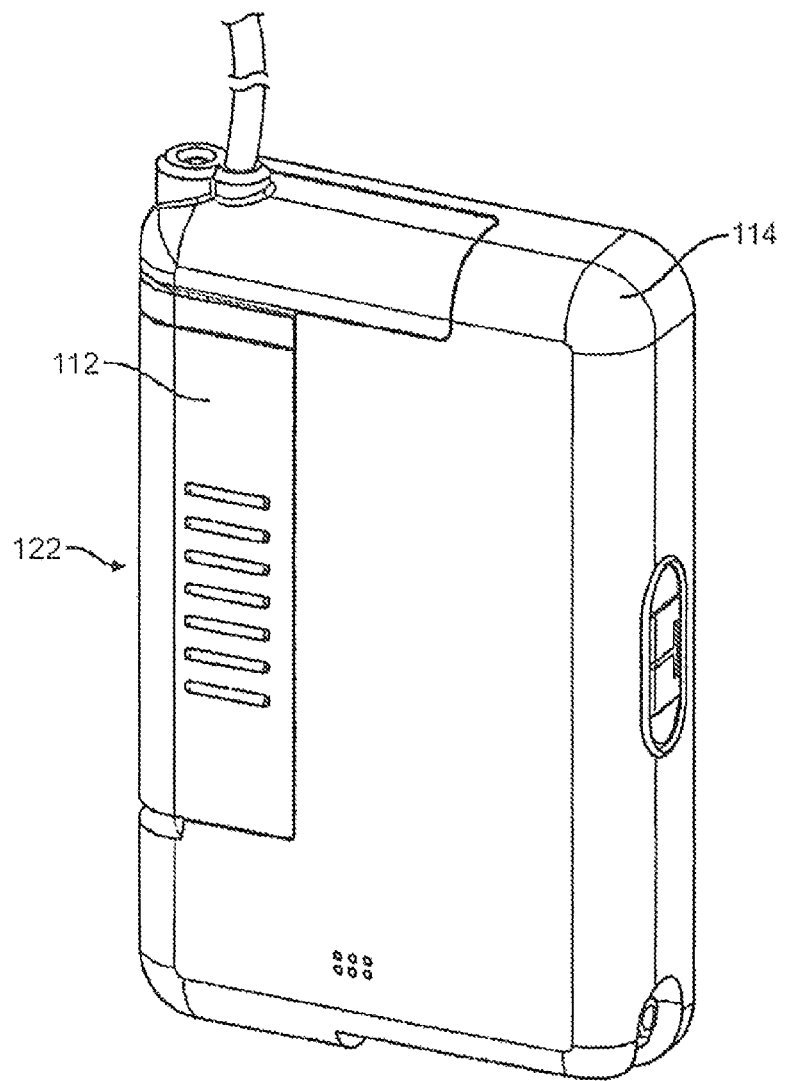
FIG. 1B is a rear perspective view of the infusion pump of FIG. 1A, including an attached infusion cartridge.

FIGS. 1A-1D depicts an embodiment of a portable infusion pump system 110 including an infusion cartridge 112 and pump device 114. Infusion cartridge 112 can be a reversibly removable and interchangeable element that may be inserted into different pump devices. Referring to FIG. 1A, a front view of the pump device 114 is depicted and includes a user friendly user interface 116 on a front surface 118 of the pump device 114. The user interface 116 includes a touch sensitive screen 120 that may be configured to display a variety of screens used for displaying data, facilitating data entry by a patient, providing visual tutorials, as well as other interface features that may be useful to a patient operating the pump device 114. FIG. 1B is a rear view of the pump device 114 and illustrates the detachable installment of the infusion cartridge 112 in a slot 122 of the pump device 114 which is configured to accept the cartridge 112.

Figure 1C:
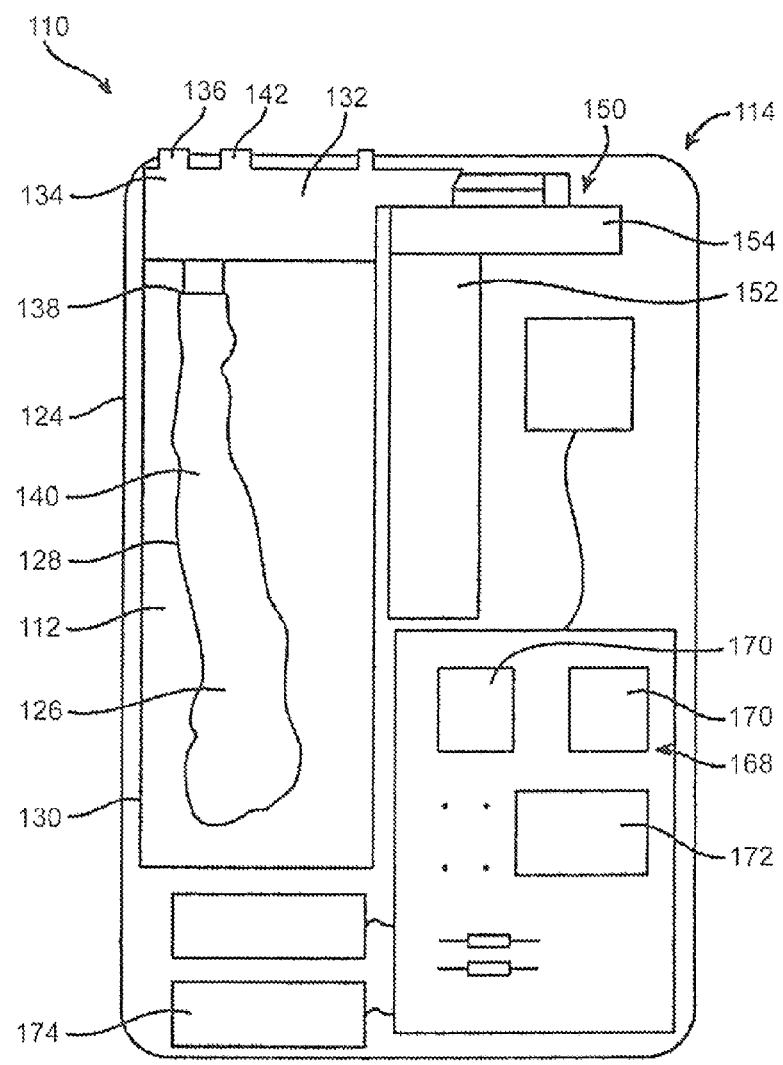
FIG. 1C is a rear schematic view of an interior of the infusion pump and cartridge embodiments of FIGS. 1A and 1B.

FIG. 1C is a schematic view of an open housing 124 of the pump device 114 depicting components that may be included in embodiments of the pump device 114. The cartridge 112 may include a fluid interface configured to receive a fluid such as collapsible reservoir 126. The collapsible reservoir 126 may be formed from a flexible material or membrane 128 that is disposed about an interior volume of the reservoir 126. The cartridge 112 also includes a substantially rigid container 130 sealed around the flexible material of the collapsible reservoir 126. A disposable delivery mechanism 132 is disposed within the disposable cartridge 112 and may have a fill port 134 with a re-sealable septum 136 sealed over the fill port 134, a reservoir inlet port 138 in fluid communication with an interior volume 140 of the collapsible reservoir 126, a fluid dispense port 142 in fluid communication with a bore 144 of the delivery mechanism 132, a vent inlet port 146 and a vent outlet port 148 both in fluid communication with the bore 144. The collapsible reservoir 126 may have a bag-like structure with flexible walls that can collapse and expand depending upon the amount of material in the volume of the reservoir. The interior volume of the reservoir may be in fluid isolation from the remaining interior volume of the rigid container 130.

The cartridge 112 may be releasably and operatively secured to a housing 124 of the pump device 114. The housing 124 may be configured to house a drive mechanism 150 including a motor 152 and gear box 154 disposed in the housing 124 and detachably coupled to a spool member 156 of the delivery mechanism 132. At least one pressure sensor 158 may be disposed in a volume 160 between an outside surface 162 of the flexible material or membrane 128 of the collapsible reservoir 126 and an inside surface 164 of the substantially rigid shell or case 130. The graphic user interface 116 may be operatively coupled to a controller 168, which may include at least one processor 170, a memory device 172 and connective circuitry or other data conduits that couple the data generating or data managing components of the device. A power storage cell in the form of a battery 174 that may be rechargeable may also be disposed within the housing 124. Data generating or managing components of the device may include the processor(s) 170, the memory device 172, sensors 158, including any pressure or temperature sensors, the GUI 166 and the like.

Figure 1D:
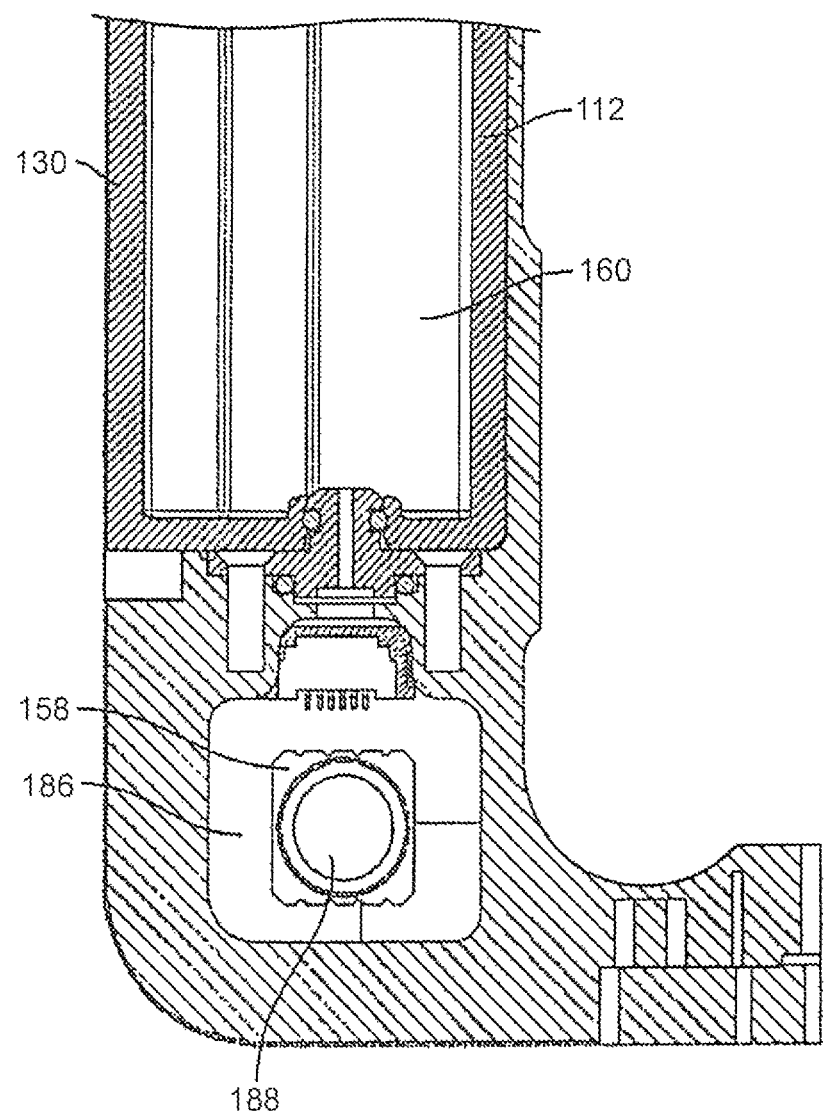
FIG. 1D is a partial sectional view of the infusion cartridge and pump device of FIGS. 1A and 1B.

The pressure inside the infusion cartridge 112, and particularly the vented volume 160 of the infusion cartridge 112, may be measured by a pressure sensor 158 disposed in the infusion cartridge 112 or in the pump device 114 in a volume, such as pocket 186 as shown in FIG. 1D. Pocket 186 is an interior volume disposed within the pump device 114 and in fluid communication with an interior volume of the fluid cartridge 112. The pocket 186 is in sealed relation with the interior volume 160 of the cartridge. As such, a pressure sensor 158 disposed within the volume of the pocket 186 will read the pressure of the volume 160 in the cartridge, but can remain with the pump device 114 after disposal of the disposable cartridge 112. This configuration lowers the cost of the cartridge while providing for pressure measurement within the cartridge 112. In some embodiments, data from the pressure sensor 158 may be used to provide a measurement of how much insulin or other medicament is being delivered by the first pump device 114. Alternatively, the pressure sensor 158 can be disposed within the cartridge directly in the vented volume 160.

The pump device 114 can also include a thermistor or other temperature sensor 188 including an optical or infrared sensor that measures the temperature of the insulin or other medicament within the reservoir 126 upon coupling the infusion cartridge 112 with the pump device 114. Taking the temperature of the air may be important in measuring how much insulin or other medicament is in the fluid reservoir. In some embodiments, the thermistor or other temperature sensor 188 is positioned in the pocket 186 such that it can measure the temperature of the air in the pocket 186 as shown in FIG. 1D. As noted above, the pocket 186 may also include a pressure sensor 158 coupled to the controller 168 for measuring pressure within the pocket 186 and volume 160. Because the air in the pocket 186 is in fluid communication with the residual air within the chamber 160, the temperature and pressure of the air in the infusion cartridge 112 surrounding the fluid reservoir 126 may be equal or approximately equal to the temperature and pressure of the air in contact with the temperature sensor 188 and pressure sensor 158. In turn, the temperature sensor 188 may provide a relatively accurate measurement of the temperature of the insulin or other medicament within the reservoir 126.

Referring to FIGS. 2-7, an embodiment of the delivery mechanism 132 is depicted in a fluid delivery cycle sequence wherein fluid from the interior volume of the reservoir 126 is drawn into the bore 220 of the delivery mechanism 132 and dispensed from the dispense outlet port 142.

Referring again to FIG. 2, a portion of the fluid reservoir cartridge 112 including a delivery mechanism 132 is shown in section as well as a portion of a drive mechanism 150 of an infusion pump. The disposable fluid cartridge 112 includes the delivery mechanism 132 which has a delivery mechanism body 236 and a bore 220 disposed in the delivery mechanism body 236. The bore 220, which may have a substantially round transverse cross section, includes a distal end 238, a proximal end 240 disposed towards the drive mechanism 150 of the infusion pump 114, an interior volume 242, a reservoir inlet port 138, a fluid dispense port 142, a vent inlet port 146 and a vent outlet port 148. The spool 156, which may also have a substantially round transverse cross section, is slidingly disposed within the bore 220 and forms a collapsible first volume 244 and a vent second volume 246 between the bore 220 and an outside surface 266 of the spool 156.

The collapsible first volume 244 of the delivery mechanism 132 may be positionable to overlap the reservoir inlet port 138 independent of an overlap of the fluid dispense port 142. The collapsible first volume 244 may be formed between a first seal 248 around the spool 156, a second seal 250 around the spool, an outer surface of the spool body between the first and second seal 250 and an interior surface 252 of the bore 220 between the first and second seal 248 and 250. The first and second seals 248 and 250 are axially moveable relative to each other so as to increase a volume of the collapsible volume 244 when the first and second seals 248 and 250 are moved away from each other and decrease the collapsible volume 244 when the seals 248 and 250 are moved closer together.

The second seal 250 is disposed on a main section 254 of the spool 156 of the delivery mechanism 132 and moves in conjunction with movement of the rest of the spool. A proximal end 196 of the spool 156 is coupled to a ball portion 194 of a drive shaft 190 of the drive mechanism 150 of the pump device 114. The drive mechanism 150 includes a rack and pinion 192 mechanism actuated by an electric motor 152 through a gear box 154. As such, the second seal 250 moves or translates axially in step with axial translation of the spool 156 and drive shaft 190. The first seal 248, however, is disposed on a distal section 258 of the spool 156 which is axially displaceable with respect to the main section 254 of the spool 156. The distal section of the spool 156 is coupled to the main section of the spool by an axial extension 260 that is mechanically captured by a cavity 261 in the main section 254 of the spool 156. This configuration allows a predetermined amount of relative free axial movement between the distal section 258 of the spool and the nominal main section 254 of the spool 156.

For some embodiments, a volume of a "bucket" of fluid dispensed by a complete and full dispense cycle of the spool 156 may be approximately equal to the cross section area of the bore 220 multiplied by the length of displacement of the captured axial extension of the spool 156 for the distal section 258. The complete bucket of fluid may also be dispensed in smaller sub-volumes in increments as small as a resolution of the drive mechanism 150 allows. For some embodiments, a dispense volume or bucket defined by the complete collapsible volume 244 of the delivery mechanism 132 may be divided into about 10 to about 100 sub-volumes to be delivered or dispensed. In some cases, the maximum axial displacement between the distal section and main section of the spool may be about 0.01 inch to about 0.04 inch, more specifically, about 0.018 inch, to about 0.022 inch.

Figure 2:
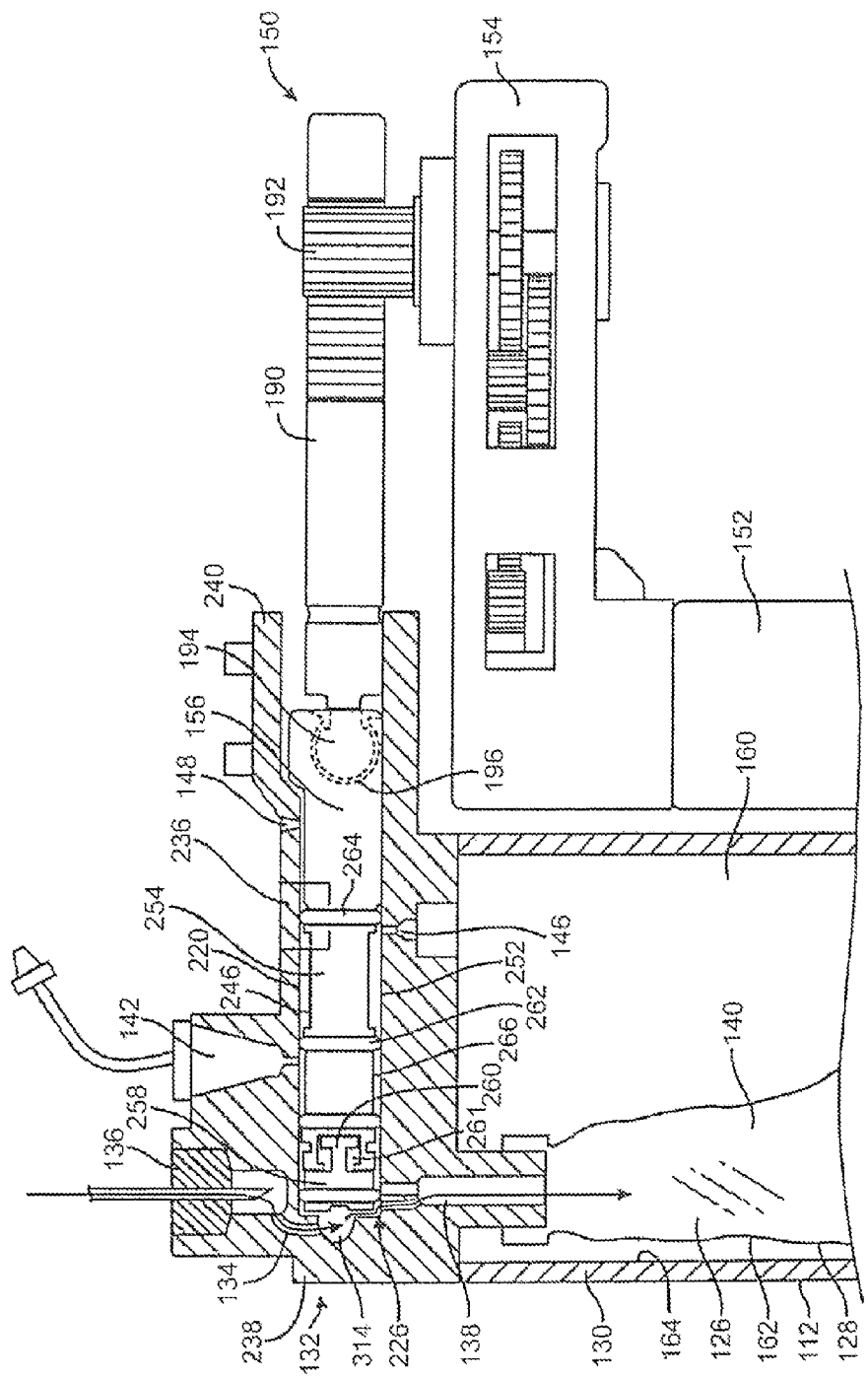
FIG. 2 is a partial sectional view of a delivery mechanism of an infusion pump with the spool of the delivery mechanism positioned at a distal hard stop for filling of the expandable reservoir according to an embodiment of the present invention.

In use, once the reservoir cartridge 112 of the infusion pump system 110 has been installed or otherwise snapped into place in the slot 122 of the pump device 114, the interior volume 140 of the collapsible reservoir 126 may then be filled with a desired fluid 121 for dispensing. In order to fill the reservoir 126, the spool 156 may be translated by the drive mechanism 150 to a hard stop position 226 as shown in FIG. 2. In the hard stop position 226 the first seal 248 is disposed proximally of a relief port 310, the relief port 310 being disposed in fluid communication between a distal end 238 of the bore 220 and the reservoir volume 140. In the hard stop position, the first seal 248 is also disposed distally of the reservoir inlet port 138. In the hard stop position, a distal end 316 of the spool 156 is contacting the distal end 238 of the bore 220 or a shoulder portion 312 of the distal end 238 of the bore 220 to prevent any further distal displacement of the spool 156.

A reservoir fill port 134 is disposed on a top portion of the bore 220 substantially opposite the bore 220 of the reservoir inlet port 138. With the spool 156 and seals 248, 250, 262 and 264 thereof so positioned, a patient may then obtain an amount of a desired fluid to be dispensed. In some cases, if the desired fluid to be dispensed is insulin or other suitable medicament, the patient 127 typically stores the insulin in a refrigerated glass container. The insulin is then accessed with a hypodermic needle 222 of a syringe device and drawn into an interior volume of the syringe (not shown). The tip of the hypodermic needle 222 of the syringe may then be pushed through a septum membrane 136 that seals the reservoir fill port 134 as shown and fluid manually dispensed from the interior volume of the syringe, through the hypodermic needle 222, through a bubble trap volume 314 in the bore 220 of the delivery mechanism 132 and into the interior volume 140 of the collapsible reservoir 126 of the cartridge 112 as shown by the arrow 318 in FIG. 2.

As discussed above with regard to other embodiments of the delivery mechanism 132, the vented volume 160 of the cartridge 112 disposed between an outside surface 162 of the flexible membrane 128 of the collapsible reservoir 126 and an inside surface 164 of the rigid shell 130 may include or be in operative communication with a pressure sensor 158. The pressure sensor 158 may be used to monitor the pressure within the vented volume 160 during the filling of the collapsible reservoir 126. The controller 168 of the pump system 114 may be programmed with information regarding the fixed volume of the rigid shell 130 of the cartridge 112 and configured to calculate the volume of fluid loaded into the collapsible reservoir 126 based on the pressure rise within the rigid shell 130 upon filling of the collapsible reservoir 126. The data regarding the volume of fluid loaded into the collapsible reservoir 126 may be stored and used to calculate and display data later in the use cycle such as fluid remaining in the collapsible reservoir 126 and the like.

Once the collapsible reservoir 126 contains a desired amount of a fluid 121 to be dispensed, a dispense cycle may be initiated by driving the spool 156 with the drive mechanism 150 based on commands from a controller 168 of the pump device to a position with the collapsible first volume 244 in communication with the reservoir inlet port 138. The hard stop position depicted in FIG. 2 is such a position. If the spool 156 has been driven to this hard stop position 226 in a distal direction from previous proximal position, the friction generated between the first seal 248 of the spool 156 and the inside surface 252 of the bore 220 will have collapsed the collapsible volume 244 of the delivery mechanism 132 with the first seal 248 and second seal 250 in a least axially separated state. In this state, the collapsible volume 244 has a minimum volume. Such a state of the delivery mechanism 132 is shown in FIG. 2. Once in this pre-fill position, the spool 156 may then be driven so as to axially separate the first and second seals 248 and 250 (and the main section 254 of the spool 156 and distal section 258 of the spool 156) of the collapsible first volume 244 and draw fluid into the first volume 244 through the reservoir inlet port 138 from the reservoir 126 as shown by the arrow 320 in FIG. 3. As the fluid 121 is drawn into the collapsible volume 244, the pressure within the vented volume 160 decreases. As previously discussed, this drop in pressure may be used in accordance with the ideal gas law to determine the amount of material taken from the collapsible reservoir 126. An unexpected reading based on the magnitude of the translation of the main section 254 of the spool 156 may also be used to detect a failure of a portion of the delivery mechanism 132 in some cases.

Figure 4:
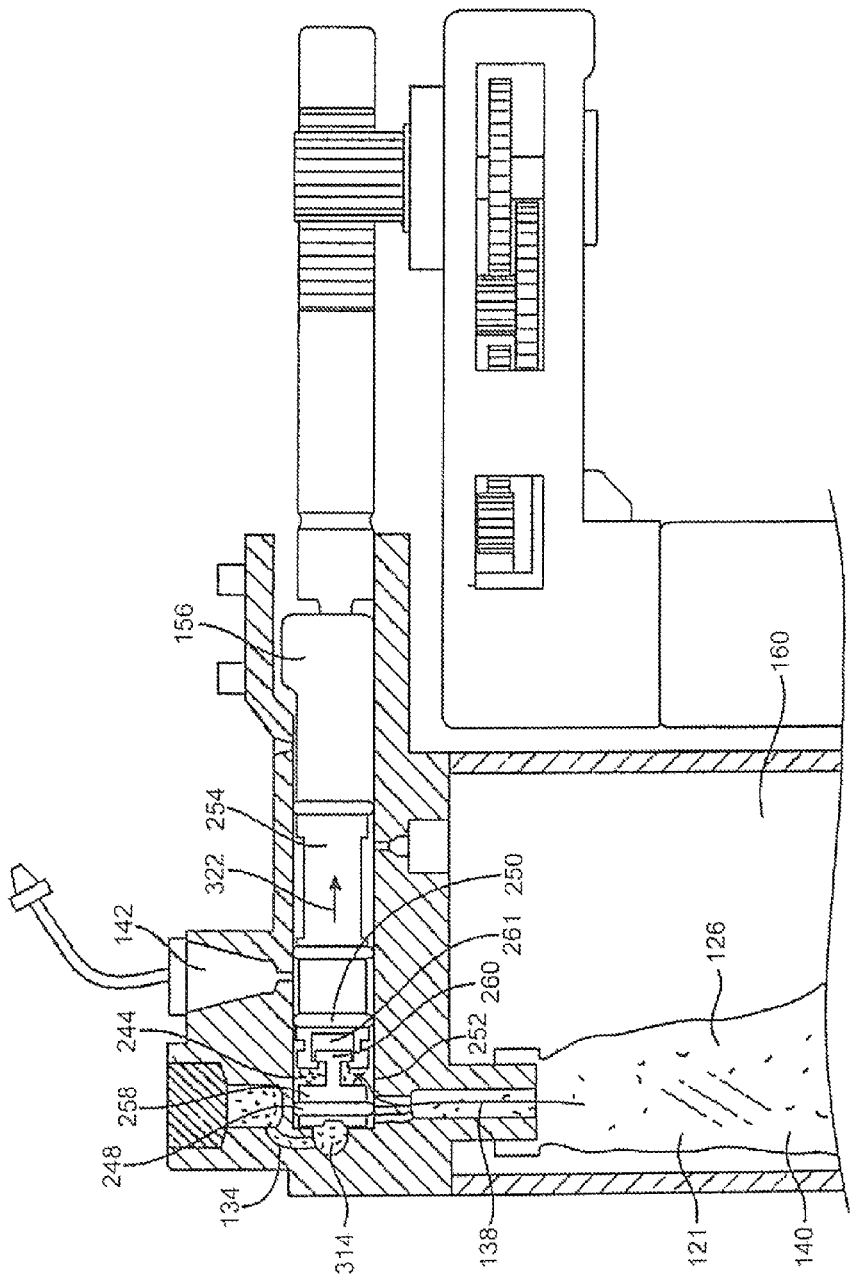
FIG. 4 is similar to FIG. 2, but with the spool of the delivery mechanism positioned after filling of the collapsible volume of the spool.
Figure 5:
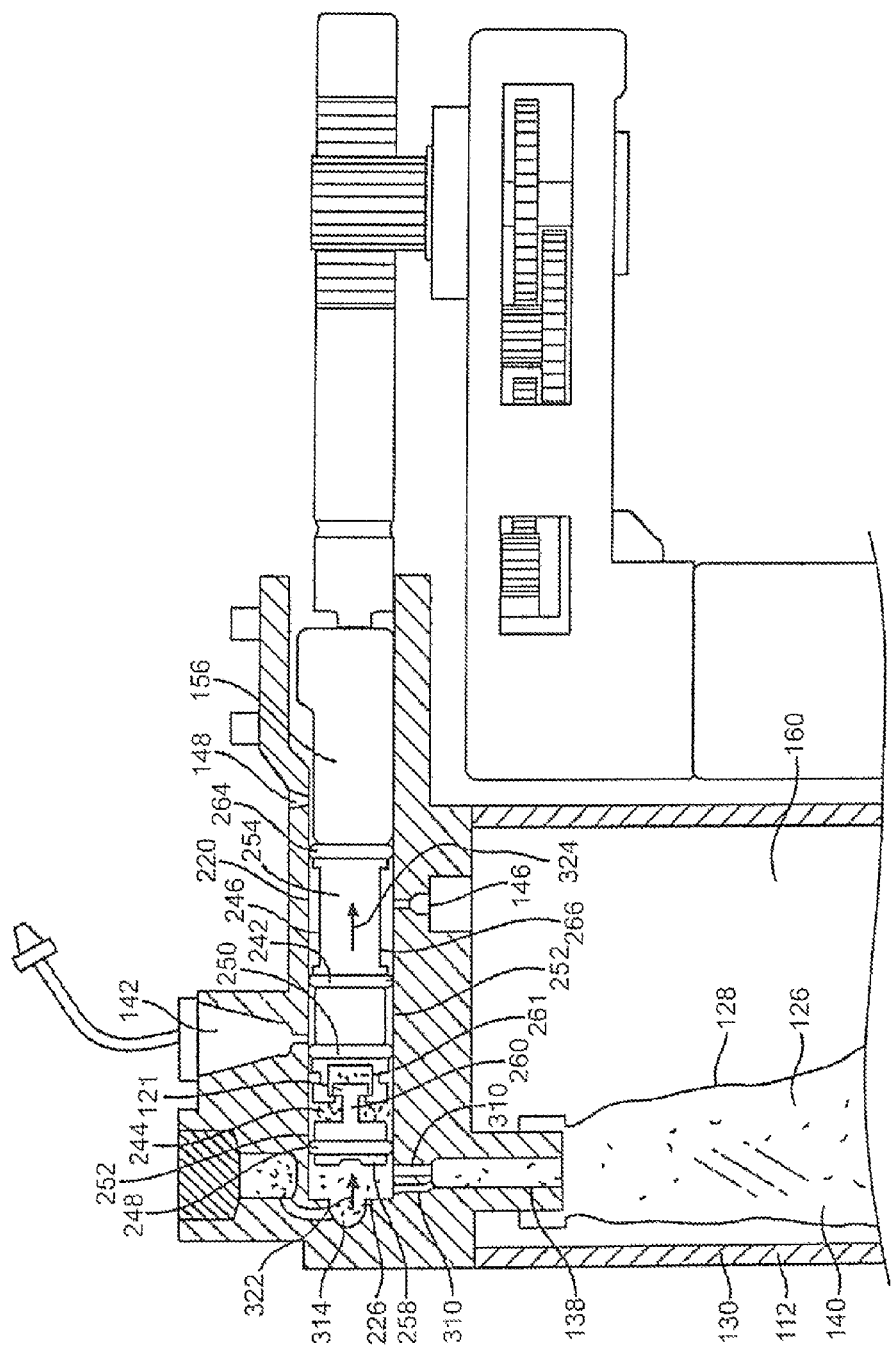
FIG. 5 is similar to FIG. 2, but with the collapsible volume of the device full of fluid being displaced proximally towards the dispense port of the device.

The collapsible volume 244 of the delivery mechanism 132 may be completely filled by proximally retracting the main section 254 and second seal 250 of the spool 156 relative to the first seal 248 and distal section 258 of the spool 156 as shown by arrow 322 on spool 156 in FIG. 4. Once filled, the spool 156 may then be driven in a proximal direction as shown in FIG. 5 wherein there are two seals 248 and 250 disposed in the bore 220 between the reservoir inlet port 138 and relief port 310 and the dispense port 142. As shown by arrow 323 and arrow 324 in FIG. 5, both the main section 254 and distal section 258 of the spool 156 are proximally retracted together. The captured axial extension of the distal section 258 by the main section 254 pulls the distal section along without axial displacement between the main section 254 and distal section 258 of the spool 156. The dispense port may be in fluid communication with a subcutaneous portion of a patient's body. The delivery mechanism 132 always includes at least one seal 248 or 250 disposed in the bore 220 between the reservoir volume 140 and material 121 disposed therein and the dispense port 142 in order to prevent a free flow condition wherein the material 121 in the reservoir 126 is in uninterrupted communication with the patient's body.

Figure 6:
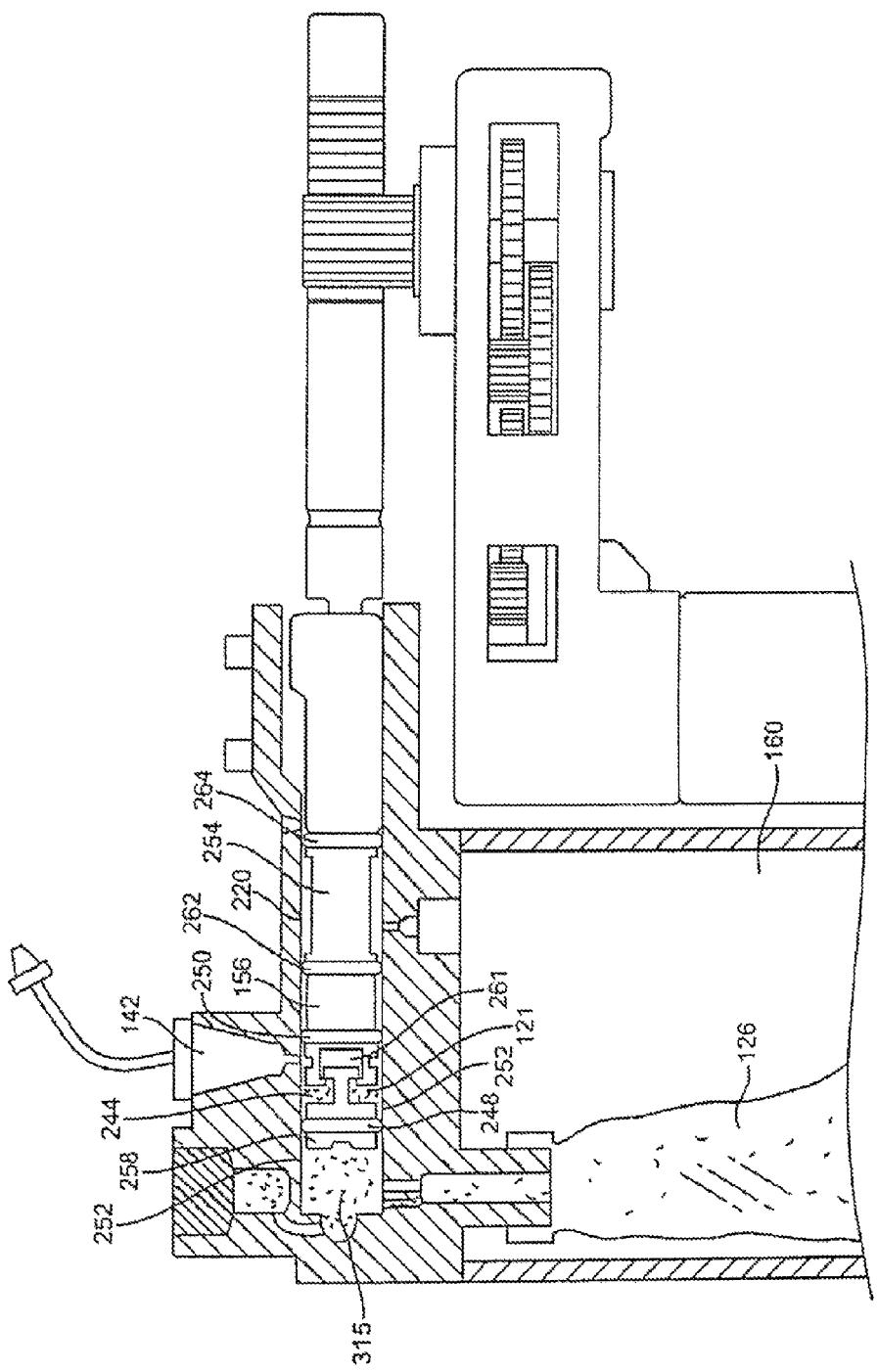
FIG. 6 is similar to FIG. 2, but with the spool of the delivery mechanism positioned prior to delivery of fluid into the dispense port from the collapsible volume of the spool.

Once filled, the spool 156 and filled collapsible volume 244 may be proximally displaced with the drive mechanism 150 to a position with the collapsible first volume 244 in communication with the fluid dispense port 142 of the bore 220 as shown in FIG. 6. Once the spool 156 is positioned as depicted in FIG. 6, the main section of the spool 156 may then be axially driven in a distal direction by the drive mechanism 150 with the distal section 258 of the spool remaining stationary or substantially stationary. This axial distal movement of the main section 254 as indicated by arrow 326 on the spool 156 depicted in FIG. 7, serves to at least partially collapse the collapsible first volume 244. Collapsing the first volume 244 of the delivery mechanism 132 dispenses fluid from the collapsible first volume 244 through the fluid dispense port 142 as shown by the arrow 328 in FIG. 7. Once all fluid from the collapsible first volume 244 is dispensed in this manner, additional cycles as described above can be completed to provide additional insulin to the patient. Further details on the operation and configuration of such an infusion pump can be found in U.S. Patent Application Publication No. 2011/0144586, which is hereby incorporated by reference herein.

The invention includes devices and methods for detecting auto dispensing and false signals related to temperature transients and mechanical forces applied to rigid container 130 cartridge as well as detection of whether collapsible reservoir 126 is at or near its maximum capacity. The methods may be implemented by processor 170 that has been programmed with an algorithm to perform the methods as described herein. Generally, processor 170 is included in an ambulatory infusion device but can be remotely located and in operable communication with the ambulatory infusion device, for example, by wireless communication.

Figure 3:
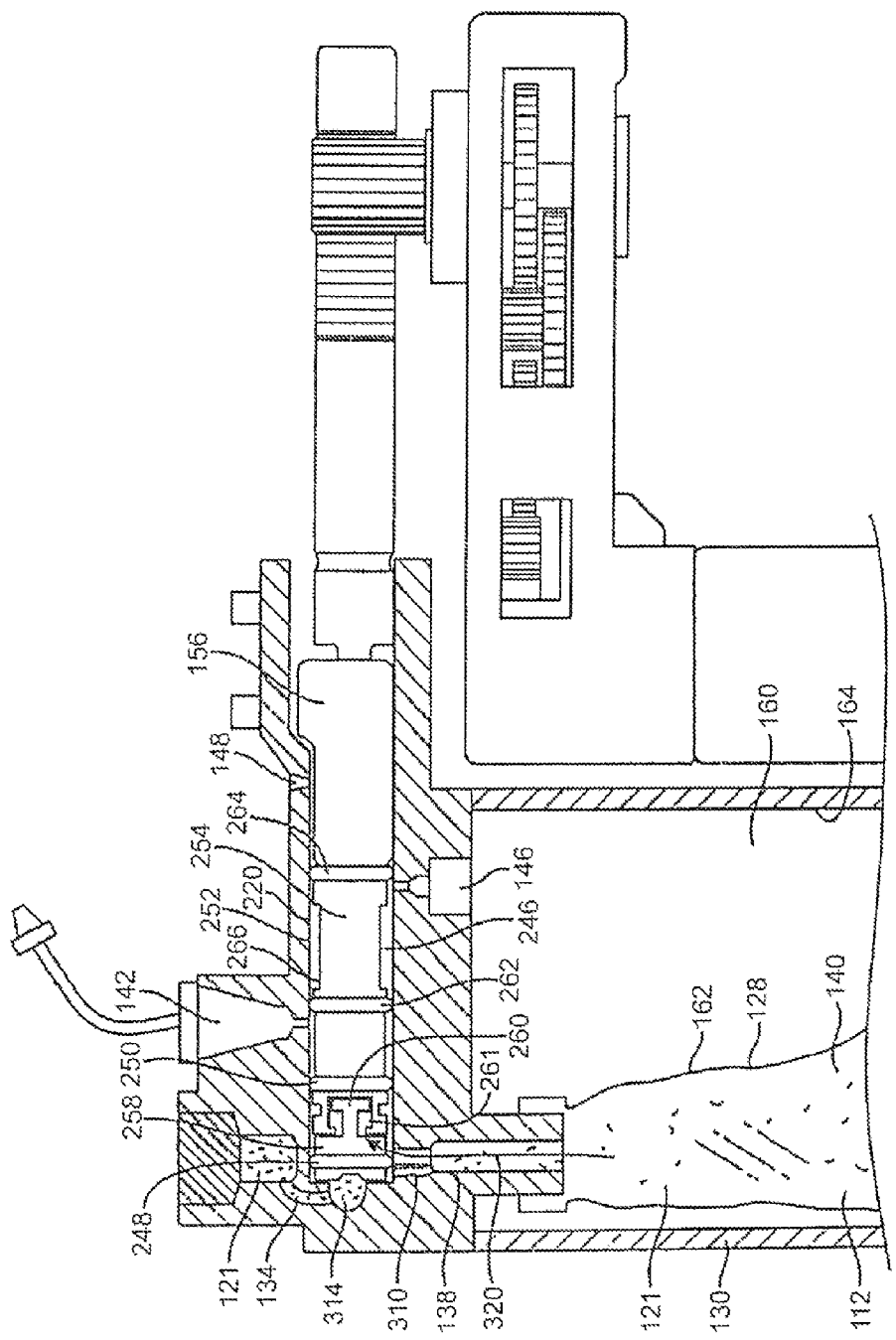
FIG. 3 is similar to FIG. 2, but with the spool of the delivery mechanism positioned for filling of a collapsible volume of the spool.
Figure 7:
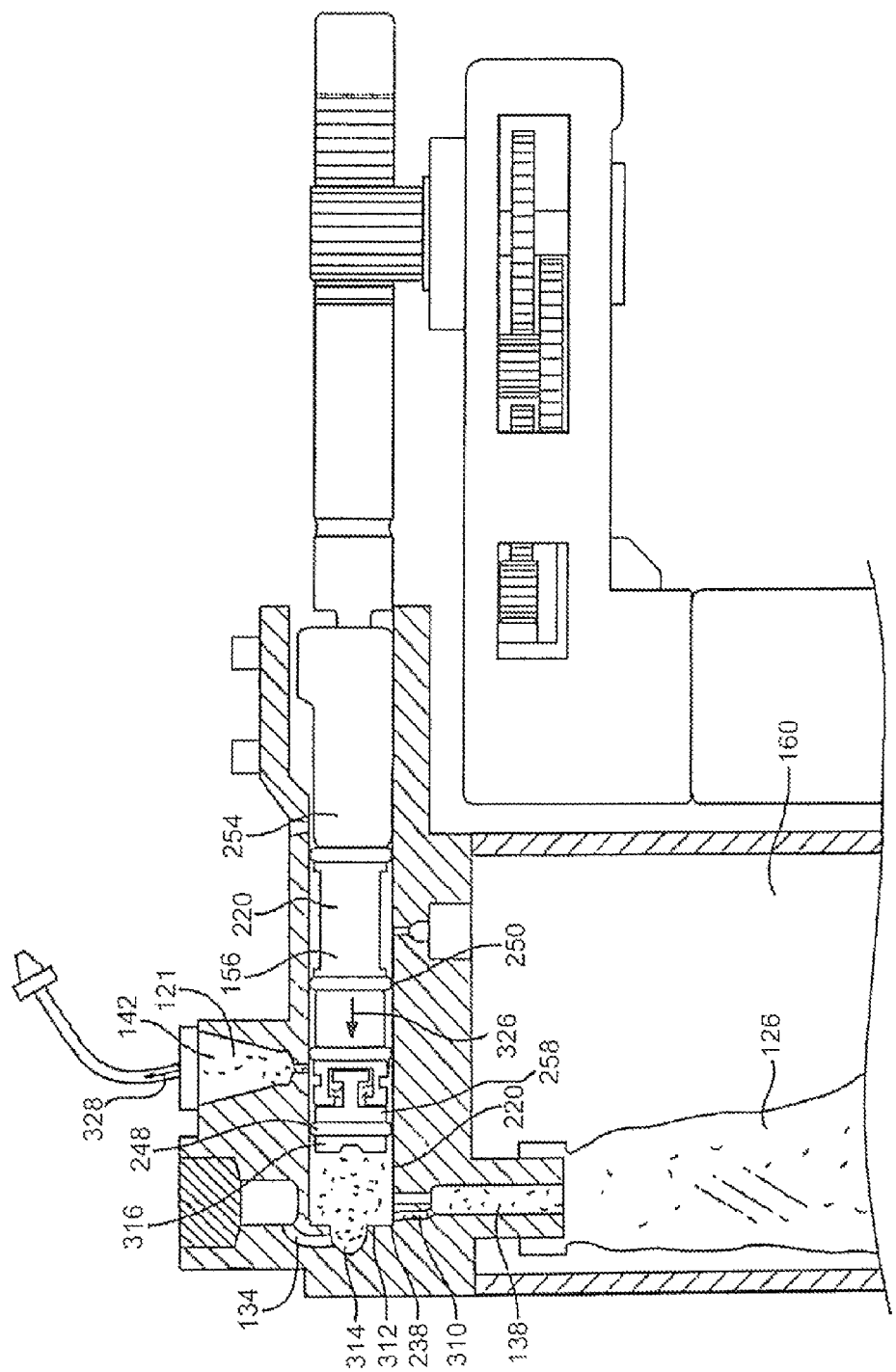
FIG. 7 is similar to FIG. 2, but with the spool of the delivery mechanism positioned after delivery of fluid from the collapsible volume of the spool into the dispense port.

Referring particularly to FIG. 3, when spool 156 is moved to distal end 238 of bore 220, spool 156 is in the ready to fill (RTF) position. Referring to FIG. 4, when main section 254 of spool 256 is moved toward a proximal end 240 of bore 220, spool 156 is in the fill position. As main section 254 of spool 156 continues to move toward proximal end 240 of bore 220, spool 156 moves toward the ready to dispense (RTD) position. This movement is depicted in FIG. 5. Referring to FIG. 6, when the spool has reached the ready to dispense position, collapsible first volume 244 is in fluid communication with fluid dispense port 142. Referring to FIG. 7, in normal operation, when main section 254 of spool 256 moves distally toward distal section 258, distal section 258 remains stationary because of friction with bore 220 and dispensing occurs when fluid is forced out through fluid dispense port 142 and spool 156 is then in the dispensed position.

In some circumstances, generally when collapsible reservoir 126 is filled to or near its maximum level or capacity and the flexible walls of collapsible reservoir 126 are under tension, excess pressure in collapsible reservoir 126 may overcome the frictional resistance to movement between bore 220 and distal section 258. In this event, distal section 258 moves toward main section 254 and fluid within collapsible first volume 244 is discharged through fluid dispense port 142. This is an undesirable event. When this event has occurred, it is said that "autodispensing" has occurred. Autodispensing causes a "bucket volume" of insulin or other fluid to be discharged when it is not intended to be discharged. Accordingly, detection of autodispensing is another aspect of the invention.

Pressure sensor 158 is used to sense pressures at regular time intervals based on air in volume 160. Autodispensing generally occurs when collapsible reservoir 126 is filled to or near its maximum level or capacity. The inventors have observed that when spool 156 moves to the RTD position, there is a period of time after the move during which pressure readings of pressure sensor 158 are variable. After spool 156 is in the RTD position for a period of time, the pressure readings stabilize. The inventors have observed that this phenomenon is significantly more pronounced in the case of a filled to or near its maximum level or capacity collapsible reservoir 126 than a partially filled collapsible reservoir 126 and can be detected by taking and evaluating pressure measurements immediately after the move to the ready to dispense position. A series of pressure measurements for a period of time are then statistically analyzed to identify standard deviation of the pressure measurement samples that occur during the time period immediately following the move to the RTD position.

Figure 9:
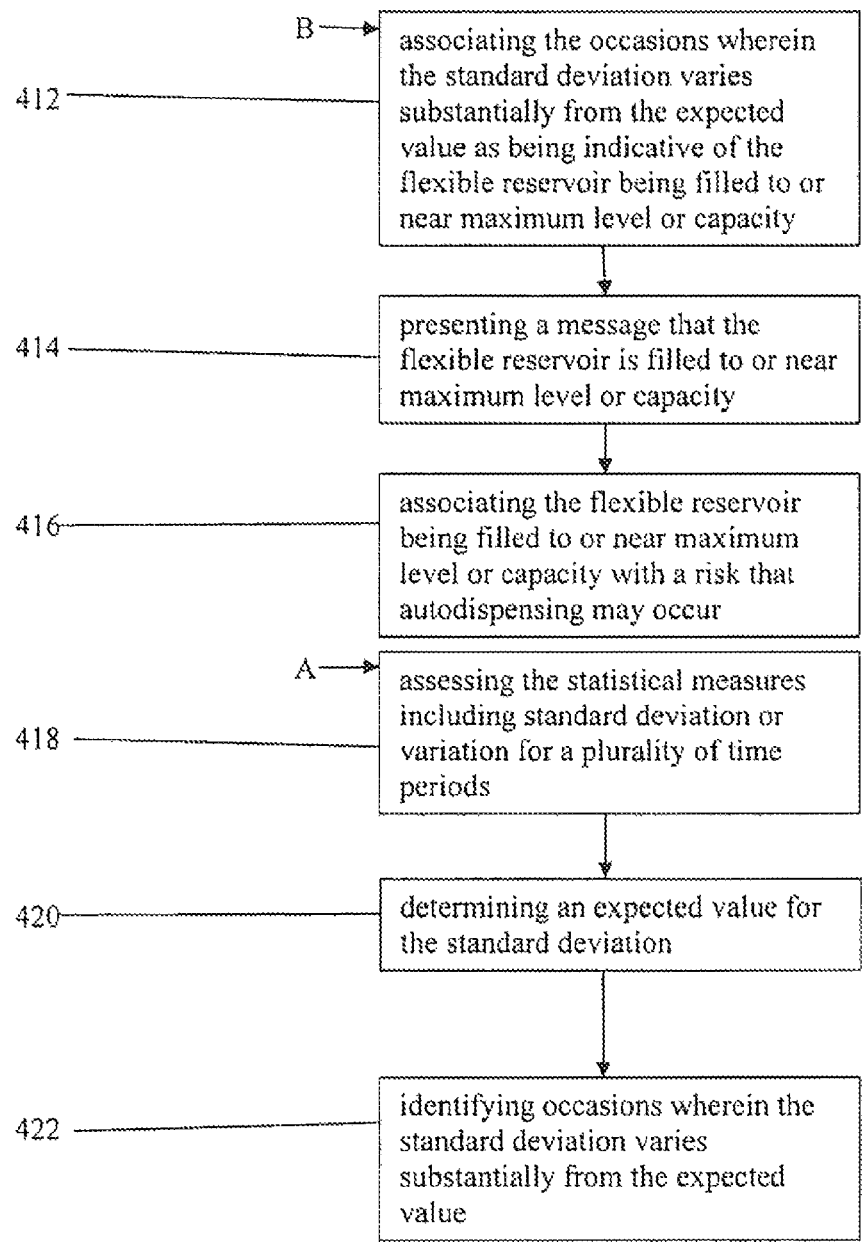
FIG. 9 is a flow chart illustrating a method according to an embodiment of the invention.
Figure 9:
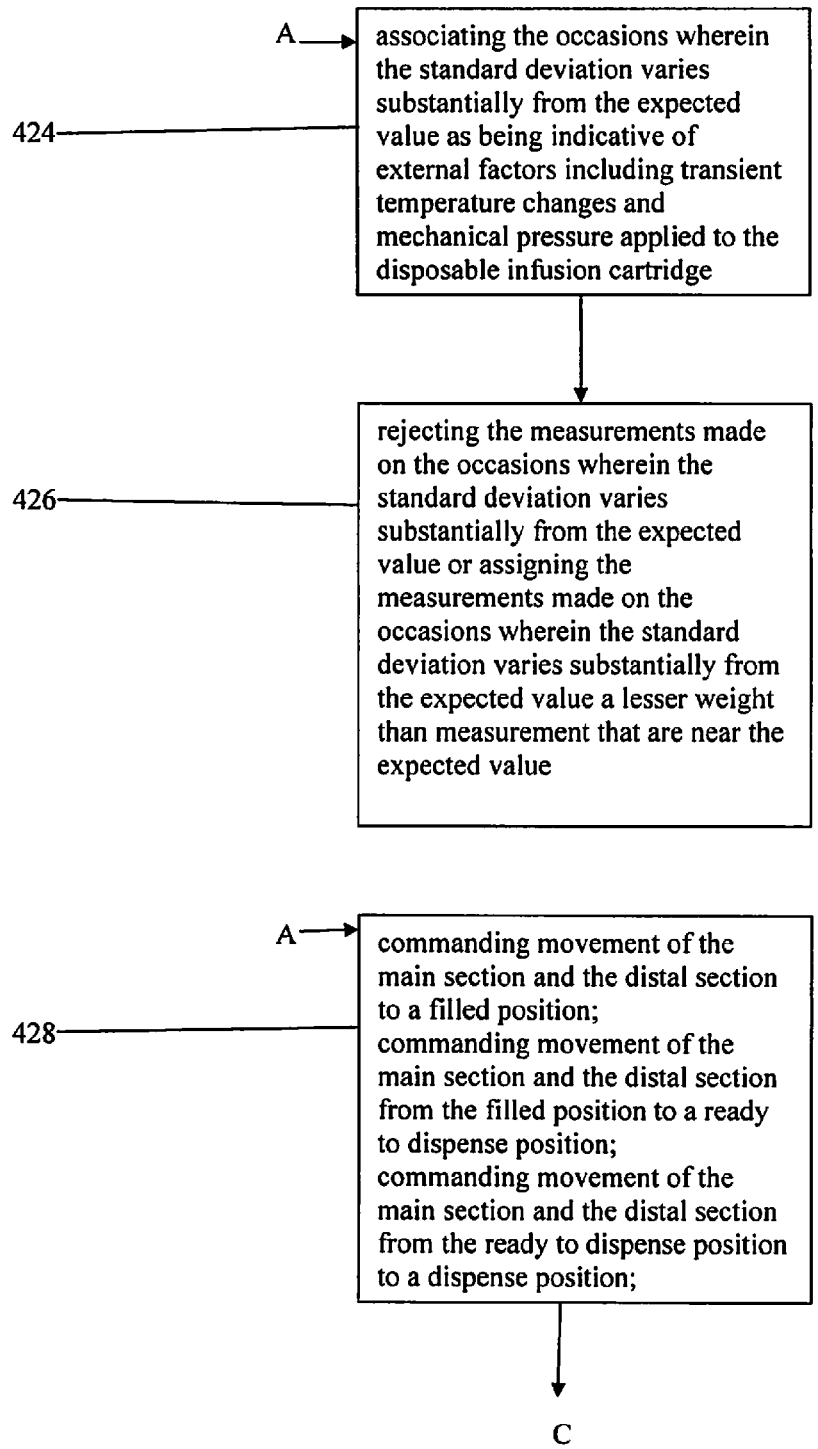
Figure 9:
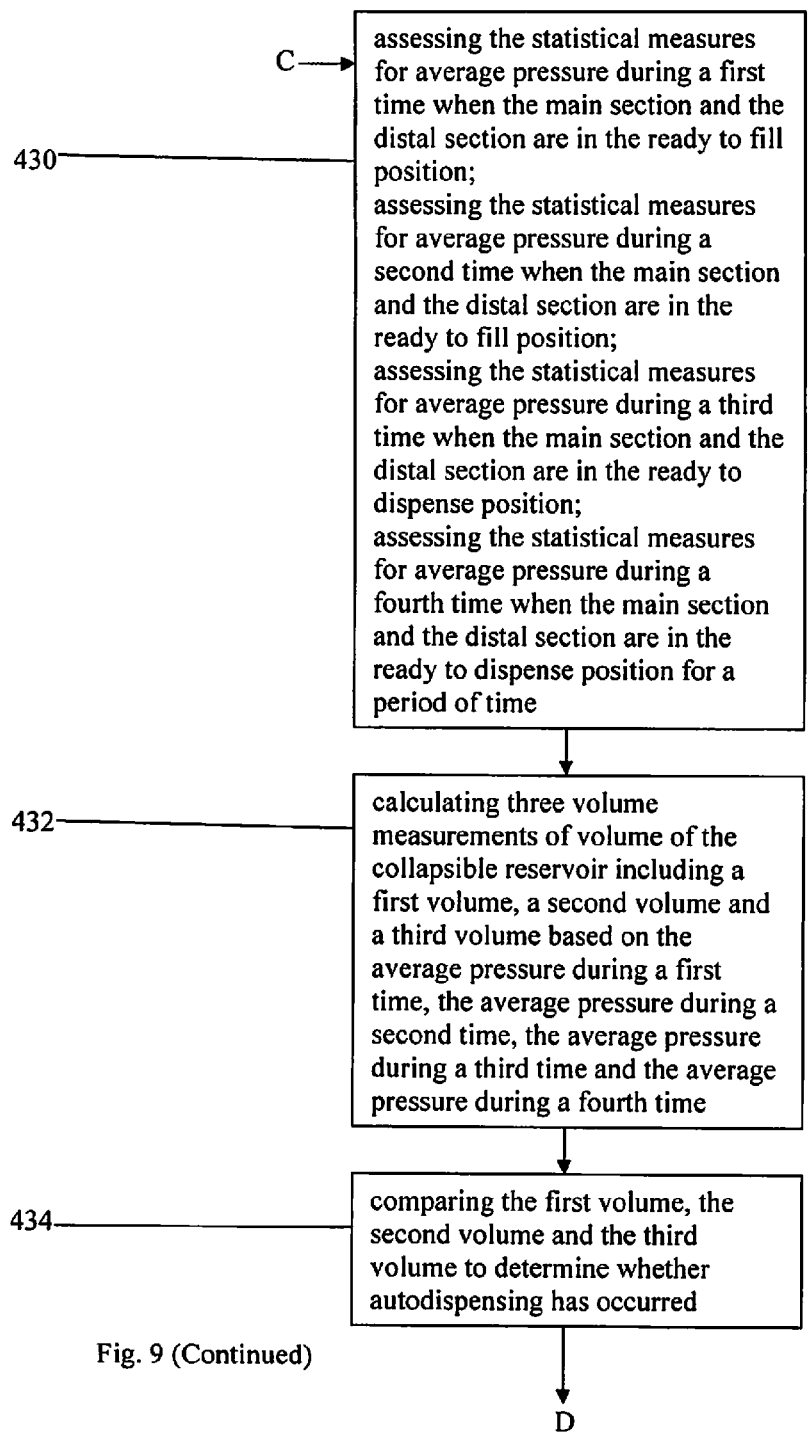
Figure 9:
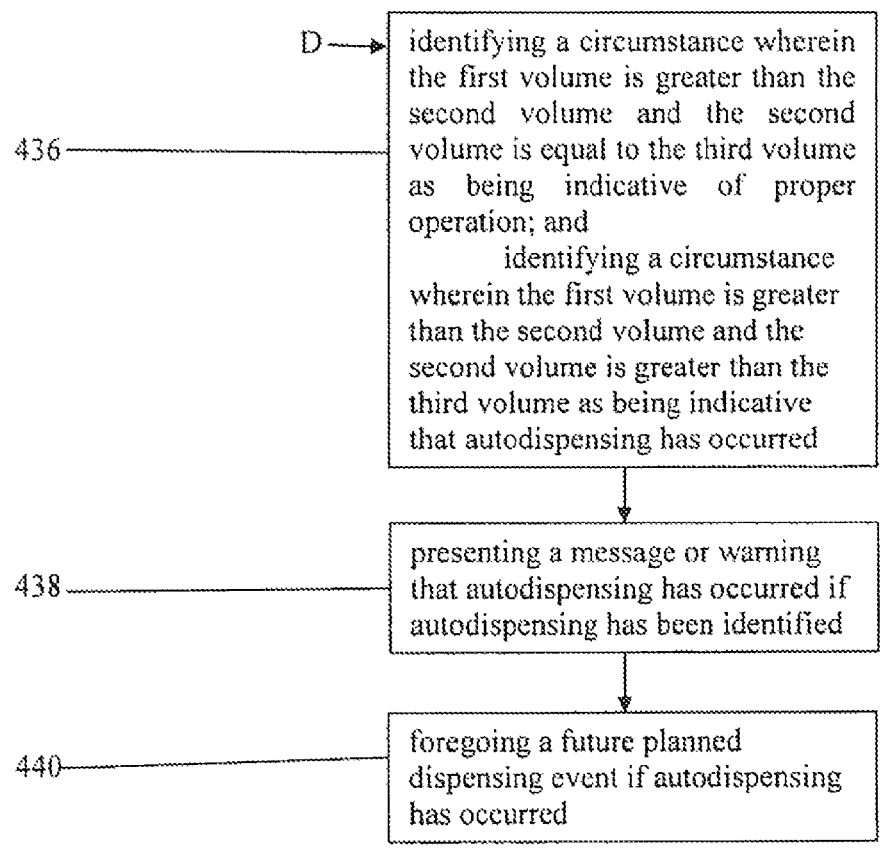

Referring to FIG. 9, according to one embodiment of the invention, a method includes actuating the pressure sensor to take pressure measurements at regular time intervals at step 400; periodically assessing a pre-selected number of the pressure measurements with statistical analysis to identify statistical measures associated with the pressure measurements at step 402; and using the statistical measures to assess the status of the flexible reservoir of the pump device at step 404.

According to another embodiment of the invention, the method includes commanding movement of spool 156 and distal section 258 to ready to dispense position at step 405. The method further includes assessing the statistical measures taken during the time following the movement of the spool and the distal section to the ready to dispense position, including calculating a standard deviation for a plurality of time periods following a plurality of movements of the spool and distal section to the ready to dispense position 406 and determining an expected value for the standard deviation at step 408. The invention further includes identifying occasions wherein the standard deviation varies substantially from the expected value at step 410.

According to another embodiment, the invention includes associating the occasions wherein the standard deviation varies substantially from the expected value as being indicative of the flexible reservoir being filled to or near its maximum level or capacity at step 412. According to another embodiment of the invention, the method may include presenting a message that the flexible reservoir is filled to or near its maximum level or capacity at step 414. According to another embodiment, the method may include associating the flexible reservoir being filled to or near its maximum level or capacity with a risk that autodispensing may occur 416.

Occasions wherein the standard deviation vary substantially from the expected value can also in some embodiments indicate the effect of external factors such as transient temperature changes or mechanical pressure applied to ridged container 130. According to another embodiment of the invention, the method may include assessing statistical measures, including standard deviation for a plurality of time periods at step 418; determining an expected value for the standard deviation at step 420; and identifying occasions wherein the standard deviation vary substantially from the expected value at step 422.

According to another embodiment, the method may include associating the occasions wherein the standard deviation vary substantially from the expected value as being indicative of external factors including transient temperature changes and mechanical pressure applied to rigid container 130 identified in the flow chart as step 424 and rejecting measurements made on occasions when the standard deviation of the pressure measurements made during a selected period of time varies substantially from the expected value. A plurality of air pressure measurements are made during a selected period of time and averaged to determine an air pressure value for that period. A standard deviation is then calculated and compared to a preselected threshold or with the standard deviation of other average pressure values for other time periods. Average pressure measurements that have out of the norm standard deviations can be rejected. Alternatively, such measurements may be assigned a lesser weight, or significance, than measurements that are near the expected value at step 426.

According to another embodiment of the invention, the method includes commanding movement of main section 254 and distal section 258 to a filled position; commanding movement of main section 254 and distal section 258 from the filled position to a ready to dispense position; and commanding movement of main section 254 and distal section 258 from the ready to dispense position to a dispense position at step 428. The method may further include assessing the statistical measures for average pressure during a first time when main section 254 and distal section 258 are in the ready to fill position; assessing the statistical measures for average pressure during a second time when main section 254 and distal section 258 are in the ready to fill position; assessing the statistical measures for average pressure during a third time when main section 254 and distal section 258 are in the ready to dispense position; assessing the statistical measures for average pressure during a fourth time when main section 254 and distal section 258 are in the ready to dispense position for a period of time at step 430. The method may further include calculating three volume measurements of volume of the collapsible reservoir including a first insulin volume, a second insulin volume and a third insulin volume based on the average pressure measured by pressure sensor 158 during a first time period or interval, the average pressure measured by pressure sensor 158 during a second time period or interval, the average pressure during a third time period or interval and the average pressure measured by pressure sensor 158 during a fourth time period or interval at step 432 and comparing the first insulin volume, the second insulin volume and the third insulin volume to determine whether autodispensing has occurred at step 434.

According to another embodiment, the invention includes identifying a circumstance wherein the first insulin volume is greater than the second insulin volume and the second insulin volume is equal to the third insulin volume as being indicative of proper operation; further it may include identifying a circumstance wherein the first insulin volume is greater than the second insulin volume and the second insulin volume is greater than the third volume as being indicative that autodispensing has occurred at step 436.

According to another embodiment of the invention, the method may include presenting a message or warning that autodispensing has occurred if autodispensing has been identified at step 438.

According to another embodiment of the invention, the method further includes foregoing a future plan dispensing event if autodispensing has occurred at step 440.

According to another embodiment of the invention, a pressure measurement is taken by the pressure sensor 158 after distal section 258 and main section 254 are in the ready to dispense position for a period or interval of time. Under normal operating conditions, it is expected that there should be no change in volume. However, if autodispensing has occurred, a reduction in volume of the collapsible reservoir 126 will have occurred indicating that autodispensing has happened.

According to another embodiment of the invention, another volume measurement is determined after dispensing has occurred. Under normal conditions there will be little or no measurable change in volume of the collapsible reservoir during this dispensing, as distal section 258 remains stationary. However, if autodispensing has occurred, distal section 258 typically will be abutted against main section 254, and an increase of volume of collapsible reservoir 126 will occur as distal section 258 and main section 254 move toward distal end 238 together.

According to an embodiment of the invention, a first pressure measurement is taken when spool 156 and distal section 258 are at the RTF or filled position. This pressure is designated P1 P1 (also designated Prtf in Equation 1). Spool 156 and distal section 258 are then moved to the RTD position. This movement causes a change in volume referred to as Delta V1. A second pressure measurement is then taken when spool 156 and distal section 258 are at the RTD position. This pressure is designated P2 (also designated Prtd in Equations 1 and 3). Spool 156 is then moved from the RTD position to the dispensed position. This movement causes a change in volume referred to as Delta V2. A third pressure measurement is taken at the dispensed position. This pressure is designated P3 (also designated Pdispensed in Equation 3). Spool 156 and distal extension 258 are moved from the dispensed position back to the RTF position. A fourth pressure measurement is taken at the RTF position. This pressure is designated P4 (also designated Prtf in Equation 3).

With knowledge of the estimated pressures and volume changes, various calculations can be made.

A first estimate of air volume in the vented volume 160 can be estimated from P1, Delta V1 and P2. Once the air volume is known, fluid volume within the collapsible reservoir 126, fluid passages and the bore 220 can be estimated by subtraction of the air volume from the total known volume. The resulting fluid volume is designated Volume estimate1.

$$VRTF1 = \frac{Prtd * DeltaV1}{Prtf - Prtd} = \text{volume of air in the} \quad \text{(Equation 1)}$$
$$\text{system when the spool is in the "}RTF\text{" position}$$

$$\text{Volume } estimate1 = Vinsulin = 4100\mu l - VRTF1 \quad \text{(Equation 2)}$$

If the second pressure equals the third pressure (P2=P3) portable infusion pump system 110 may be generally considered to be operating properly because during normal dispensing the spool distal section 258 remains stationary during dispensing. If the second pressure is less than the third pressure (P2<P3) it can be inferred that either there is an occlusion in the fluid dispensing port 142 or line or that autodispensing has occurred. This is because the spool distal section 258 has moved distally thus increasing P3.

A second estimate of air volume in the vented volume 160 can be estimated from P3, Delta V2 and P4. Once the air volume is known, fluid volume within collapsible reservoir 126, fluid passages and bore 220 can be estimated by subtraction of the air volume from the total known volume. The resulting fluid volume is designated Volume estimate2.

$$VRTF2 = \frac{Pdispensed * DeltaV3}{Prtf - Pdispensed} = \text{volume of air in the system when the spool is in the "RTF" position} \quad \text{(Equation 3)}$$

$$\text{Volume } estimate2 = Vinsulin = 4100\mu l - VRTF2 \quad \text{(Equation 4)}$$

Based on the above information the following can be estimated:

If the second pressure equals the third pressure (P2=P3), portable infusion pump system 110 may be generally considered to be operating properly.

If the second pressure is less than the third pressure (P2<P3) and Volume estimate1 is less than Volume estimate2, it can be inferred that portable infusion pump system 110 has autodispensed because the fill estimate has decreased.

If the second pressure is less than the third pressure (P2<P3) and Volume estimate1 is equal to Volume estimate2, it can be inferred that there is an occlusion in the fluid dispensing port 142 or line because the fill estimate has not decreased. Thus, insulin is not being dispensed.

According to another embodiment, a persistence filter is included in the method so that the process is repeated a number of times before an inference is made that autodispensing has occurred or that an occlusion exists. If the process is repeated the designated number of times and it is inferred that autodispensing has occurred or that an occlusion exists, the method includes presenting a message, alarm or warning that that autodispensing has occurred or that an occlusion exists, as appropriate.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. An ambulatory infusion system, comprising:
    an infusion cartridge, the infusion cartridge including a collapsible reservoir for containing a fluid and a substantially rigid shell disposed over the collapsible reservoir and forming an interior volume between an outside surface of the collapsible reservoir and an inside surface of the shell;
    a pump device configured to selectively receive the infusion cartridge and cooperate with the infusion cartridge to deliver fluid from the reservoir to the patient;
    a pressure sensor located in one of the infusion cartridge and the pump, the pressure sensor in communication with the interior volume of the infusion cartridge; and
    a processor located in one of the infusion cartridge and the pump, wherein the processor is programmed with an algorithm to perform the following:
    actuating the pressure sensor to take pressure measurements at regular time intervals;
    periodically assessing a preselected number of the pressure measurements with statistical analysis to identify statistical measures associated with the pressure measurements including determining a standard deviation for the preselected number of the pressure measurements;
    using the standard deviation to assess the status of the flexible reservoir and the pump device including identifying occasions wherein the standard deviation varies substantially from an expected standard deviation; and
    associating the occasions wherein the standard deviation varies substantially from an expected standard deviation with the flexible reservoir being filled to or near its maximum level or capacity.

2. The ambulatory infusion system as claimed in claim 1, wherein the pump device further comprises a spool including a main section and a distal section; and
    wherein the processor is further programmed to:
    command movement of the main section and the distal section to a ready to dispense position;
    assess the statistical measures during a time following the movement of the main section and the distal section to a ready to dispense position including determining the standard deviation for a plurality of time periods following a plurality of movements of the main section and the distal section to a ready to dispense position.

3. The ambulatory infusion system as claimed in claim 1 wherein the processor is further programmed to:
    present a message that the flexible reservoir is filled to or near its maximum level or capacity upon identifying an occasion wherein the standard deviation varies substantially from the expected standard deviation.

4. The ambulatory infusion system as claimed in claim 1, wherein the processor is further programmed to:
    associate the flexible reservoir being filled to or near its maximum level or capacity with a risk that autodispensing may occur.

5. An ambulatory infusion system, comprising:
    an infusion cartridge, the infusion cartridge including a collapsible reservoir for containing a fluid and a substantially rigid shell disposed over the collapsible reservoir and forming an interior volume between an outside surface of the collapsible reservoir and an inside surface of the shell;
    a pump device configured to selectively receive the infusion cartridge and cooperate with the infusion cartridge to deliver fluid from the reservoir to the patient;
    a pressure sensor located in one of the infusion cartridge and the pump, the pressure sensor in communication with the interior volume of the infusion cartridge; and
    a processor located in one of the infusion cartridge and the pump, wherein the processor is programmed with an algorithm to perform the following:
    actuating the pressure sensor to take pressure measurements at regular time intervals;
    periodically assessing a preselected number of the pressure measurements with statistical analysis to identify statistical measures associated with the pressure measurements including determining a standard deviation for the preselected number of the pressure measurements;
    using the standard deviation to assess the status of the flexible reservoir and the pump device including identifying occasions wherein the standard deviation varies substantially from an expected standard deviation; and
    associating the occasions wherein the standard deviation varies substantially from the expected value as being indicative of external factors including transient temperature changes and mechanical pressure being applied to the disposable infusion cartridge.

6. The ambulatory infusion system as claimed in claim 5, wherein the processor is further programmed to:
    reject the pressure measurements made on the occasions wherein the standard deviation varies substantially from the expected value when determining fluid volume in the cartridge from the pressure measurements.

7. The ambulatory infusion system as claimed in claim 5, wherein the processor is further programmed to:
assign the pressure measurements made on the occasions wherein the standard deviation varies substantially from the expected value a lesser weight than pressure measurements taken when the standard deviation is near the expected value when determining fluid volume in the cartridge from the pressure measurements.

* * * * *